(12) United States Patent
List

(10) Patent No.: US 10,660,556 B2
(45) Date of Patent: May 26, 2020

(54) BODY FLUID SAMPLING ELEMENT

(71) Applicant: Roche Diabetes Care, Inc., Indianapolis, IN (US)

(72) Inventor: Hans List, Hesseneck-Kailbach (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 357 days.

(21) Appl. No.: 14/897,703

(22) PCT Filed: Jun. 10, 2014

(86) PCT No.: PCT/EP2014/061986
§ 371 (c)(1),
(2) Date: Dec. 11, 2015

(87) PCT Pub. No.: WO2014/198700
PCT Pub. Date: Dec. 18, 2014

(65) Prior Publication Data
US 2016/0143568 A1 May 26, 2016

(30) Foreign Application Priority Data

Jun. 13, 2013 (EP) .................................... 13171786

(51) Int. Cl.
*A61B 5/15* (2006.01)
*A61B 5/151* (2006.01)
(Continued)

(52) U.S. Cl.
CPC ...... *A61B 5/150068* (2013.01); *A61B 5/1477* (2013.01); *A61B 5/157* (2013.01);
(Continued)

(58) Field of Classification Search
CPC ............ A61B 5/150068; A61B 5/1477; A61B 5/150022; A61B 5/150412;
(Continued)

(56) References Cited

U.S. PATENT DOCUMENTS

| 7,223,276 B2 | 5/2007 | List et al. |
| 7,785,338 B2 | 8/2010 | Kuhr et al. |

(Continued)

FOREIGN PATENT DOCUMENTS

| CN | 1220132 A | 6/1999 |
| CN | 102695451 A | 9/2012 |

(Continued)

OTHER PUBLICATIONS

International Preliminary Report of Patentability dated Dec. 15, 2015, on PCT/EP2014/061986.
English Abstract of CN102695451A.

*Primary Examiner* — Daniel L Cerioni
(74) *Attorney, Agent, or Firm* — Woodward, Emhardt, Henry, Reeves & Wagner LLP

(57) ABSTRACT

A sampling element (110) for generating a sample of a body fluid is disclosed. The sampling element (110) comprises a housing (114), the housing having a chamber (122) with at least one puncture element (112) stored therein. A tip (132) of the puncture element (112) is movable through at least one puncture opening (124) of the housing (114) in order to perforate a skin portion of a user. The sampling element (110) further comprises at least one compression element (150), which is adapted to increase a pressure of the body fluid within a body tissue of the user in a region of puncturing when pressed onto the skin portion of the user. The compression element (150) is movably mounted to the housing (114). The sampling element (110) comprises at least one locking mechanism (168) for releasably locking the compression element (150) in at least two positions. The at least two positions comprise a first position (170) and a second position (172), the second position (172) being offset from the first position (170). In a further aspect of the invention, an analytical device (204) is disclosed, the ana- (Continued)

Figure 1:
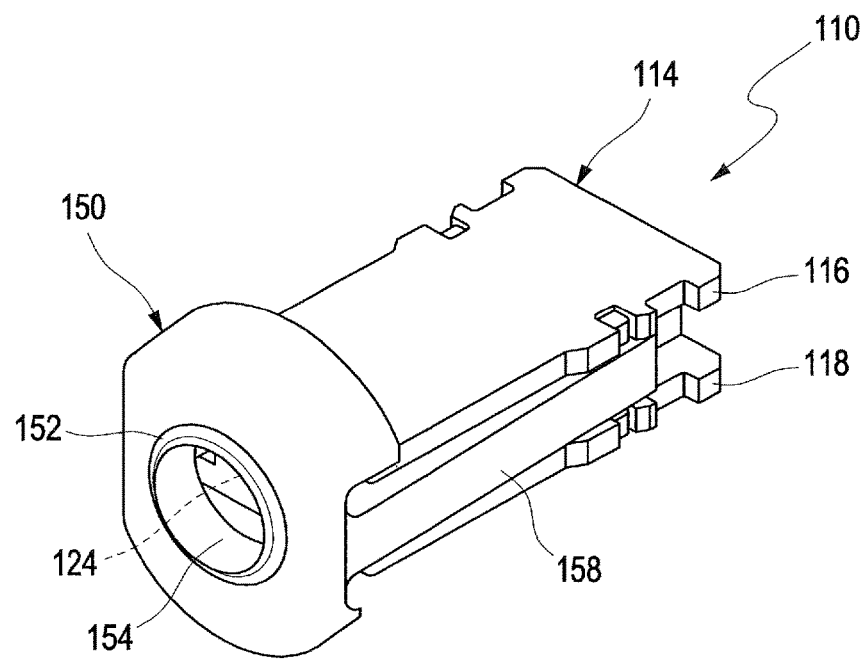

lytical device (204) being adapted for using the sampling element (110) of the invention.

17 Claims, 10 Drawing Sheets

(51) Int. Cl.
*A61B 5/157* (2006.01)
*A61B 5/1477* (2006.01)

(52) U.S. Cl.
CPC .......... *A61B 5/1513* (2013.01); *A61B 5/1519* (2013.01); *A61B 5/150022* (2013.01); *A61B 5/15111* (2013.01); *A61B 5/15113* (2013.01); *A61B 5/15117* (2013.01); *A61B 5/15142* (2013.01); *A61B 5/15194* (2013.01); *A61B 5/150412* (2013.01); *A61B 5/150503* (2013.01); *A61B 5/150893* (2013.01); *A61B 5/150916* (2013.01)

(58) Field of Classification Search
CPC ........ A61B 5/150503; A61B 5/150893; A61B 5/150916; A61B 5/15111; A61B 5/15113; A61B 5/15117; A61B 5/1513; A61B 5/15142; A61B 5/1519; A61B 5/15194; A61B 5/157
USPC ....................................................... 600/583
See application file for complete search history.

(56) References Cited

U.S. PATENT DOCUMENTS

| | | |
|---|---|---|
| 7,842,060 B2 | 11/2010 | List |
| 8,361,099 B2 | 1/2013 | Schosnig et al. |
| 9,097,679 B2 | 8/2015 | List et al. |
| 2002/0177787 A1* | 11/2002 | Duchon ............. A61B 5/14532 600/583 |
| 2007/0088377 A1* | 4/2007 | LeVaughn et al. .. A61B 5/1411 606/181 |
| 2008/0082023 A1* | 4/2008 | Deck ................ A61B 5/150022 600/583 |
| 2008/0262388 A1* | 10/2008 | List .................... A61B 5/14514 600/583 |
| 2011/0029006 A1* | 2/2011 | Leong ................. A61B 5/1411 606/182 |

FOREIGN PATENT DOCUMENTS

| | | |
|---|---|---|
| EP | 1 384 438 B1 | 5/2003 |
| EP | 1 459 683 A1 | 3/2004 |
| EP | 1 586 270 A2 | 4/2005 |
| EP | 1 669 028 A1 | 11/2005 |
| EP | 1 808 128 A1 | 1/2006 |
| EP | 1 643 908 B1 | 4/2006 |
| WO | WO 97/43962 A1 | 11/1997 |
| WO | WO 2009/145920 A1 | 12/2009 |
| WO | WO 2010/056869 A2 | 5/2010 |
| WO | WO 2011/014260 A1 | 2/2011 |
| WO | WO 2011/044971 A1 | 4/2011 |
| WO | WO 2011/084103 A1 | 7/2011 |
| WO | WO 2012089524 A1 | 7/2012 |
| WO | WO 2012/140027 A1 | 10/2012 |

\* cited by examiner

BODY FLUID SAMPLING ELEMENT

FIELD OF THE INVENTION

The invention refers to a sampling element for generating a sample of a body fluid. The sampling element preferably is adapted to provide a protection against reuse. The invention further relates to an analytical device being adapted for using the sampling element. The invention further relates to a method of generating a sample of a body fluid and to a use of a position of a compression element movably mounted to a housing of a sample element for indicating a used or unused state of the sampling element, for preventing reuse of the sampling element. The sampling element, the method and the use according to the present invention preferably may be used in the field of determining the presence and/or the concentration of one or more analytes in a body fluid such as blood, interstitial fluid or other types of body fluids. As an example, the at least one analyte may be one or more of glucose, cholesterol, lactate and triglyceride. Additionally or alternatively, however, other types of analytes may be determined. The invention may be applied both in the field of home monitoring and in the field of professional diagnostics such as in hospitals and/or intensive care institutions. Specifically, the method may be applied in the field of self-monitoring by a user or patient or by a medical assistant and may be performed without medical expert knowledge. In the following, without intending to restrict the scope of the present invention and without restricting the application of the invention in other fields, the invention will mainly be disclosed in the context of determining a concentration of glucose in blood and/or interstitial fluid.

RELATED ART

In the art of medical diagnostics, a large number of sampling elements for generating and, optionally, analyzing one or more samples of a body fluid are known, both for home monitoring and for professional care. Thus, as an example, EP 1 669 028 A1 discloses a lancing device for generating an incision in a body surface. The device comprises a housing containing a lancet, a driving rotor and a lancet coupling mechanism. Further, a specific driving cycle is disclosed. In addition, further examples of sampling elements are disclosed in WO 2011/014260 A1, EP 1 586 270 A2, WO 2009/145920 A1, WO 2010/056869 A2, and WO 97/43962 A1.

For hygienic purposes, in many cases, a protection against reuse of the sampling elements is desirable. Thus, sampling elements are known which provide appropriate mechanisms preventing reuse. As an example, EP 1 808 128 A1 discloses a puncture aid having a blocking element which is designed to prevent a reuse by preventing specific rotational motions of the puncture aid. EP 1 459 683 A1 discloses a lancet system having a protection against reuse, the lancet system comprising a needle body which protects a needle tip and provides a protection against reuse of the lancet system.

Further, in the art, a plurality of sampling systems are known which are adapted to automatically take a sample of a body fluid and, further, to provide an analytical aid for detection of one or more contents within the sample, such as a glucose content. These combined analytical aids, containing puncture elements and means for detecting at least one analyte, are known in various ways. Thus, devices and systems are known containing magazines having a plurality of coherent analytical aids in one housing, and single analytical aids which may be handled independently from each other.

Thus, generally, WO 2011/044971 A2 discloses a device for taking and analyzing a blood sample, comprising an integrated drive unit having a two drive sources and a driving force transmitting gear train, by means of which a lancet drive, an apparatus for advancing a magazine and a sample transmitting apparatus can be coupled to the drive source. A stressing rotor and a drive rotor are rotably mounted co-axially to each other. A first cam control converts the rotation of the drive rotor into a radial forward and backward motion of a driving rod. A second cam control converts the rotational motion of the stressing rotor into a linear motion of a slotted-link slider. A switching slotted-linked moved by the slotted-link slider rotates the magazine one step further. A third cam control converts the rotational motion of the stressing rotor into a linear motion of a push rod perpendicular to the pricking axis.

In WO 2012/089524 A1, a lancet housing assembly is disclosed, including a housing structure comprising multiple lancet compartments. At least one lancet compartment comprises an outer facing side and an inner facing side. A floor extends between the outer facing side and the inner facing side. A reagent material is located on the floor and within the lancing compartment. A lancet structure is located in the at least one lancet compartment. The lancet structure comprises a skin-penetrating end and a blood transport portion. The blood transport portion is arranged and configured to receive the amount of blood from the skin-penetrating end and to carry the amount of blood away from the skin side to the reagent material.

WO 2012/140027 A1 discloses both analytical aids combined in a common housing and single analytical aids which may be handled independently from each other. The document further discloses a method for producing an analytical aid, comprising at least one housing and at least one test element having at least one chemical test system.

In combined analytical devices containing a plurality of analytical aids in a magazine, protection specifically may be provided on the side of an analytical device using the magazine, such as the device disclosed in WO 2011/044971 A1. Still, even in combined analytical aids having both puncture elements and detection means for detecting an analyte, protection against reuse may cause some major technical challenges. Specifically in case single analytical aids having one puncture element stored therein, which may be handled independently from other analytical aids, protection against reuse still is a technical issue. Thus, specifically for hygienic purposes and in order to prevent damage to an analytical device using the analytical aid or sampling element, technical solutions protecting the sampling elements against reuse are highly desirable.

Problem to be Solved

It is therefore an object of the present invention to provide a sampling element and an analytical device which at least partially overcome the above-mentioned technical challenges and problems of known sampling elements and analytical devices. Specifically, a simple, easy-to-use protection against reuse shall be provided which, specifically, is applicable to single sampling elements.

SUMMARY OF THE INVENTION

This problem is solved by a sampling element, an analytical device, a method and a use according to the independent claims. Preferred embodiments which may be realized in an isolated fashion or in combination, as the skilled person will recognize, are listed in the independent claims As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context, and to a situation in which one or more further features are present. As an example, the expressions "A has B", "A comprises B" and "A includes B" may both refer to a situation in which, besides B, no other element is present in A (i.e. a situation in which a solely and exclusively consists of B) and to a situation in which, besides B, one or more further elements are present in entity A, such as element C, elements C and D or even further elements.

Further, as used in the following, the terms "preferably", "more preferably", "most preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect of the present invention, a sampling element for generating a sample of a body fluid is disclosed. As used herein, a sampling element, also referred to as an analytical aid, a puncture aid or a pricking aid, generally refers to an arbitrary element which is adapted to generate a sample of the body fluid by perforating a skin portion of a user, such as by lancing, pricking or cutting. Thus, specifically, the sampling element comprises a puncture element such as a lancet and/or needle.

The sampling element, as will be outlined in further detail below, preferably is a single sampling element, also referred to as a single test, which contains precisely one puncture element and which may be handled in an isolated fashion, independently from other sampling elements. Thus, specifically, the sampling element may have precisely one housing with precisely one chamber and/or puncture element contained therein, without any further puncture elements and/or chambers, as opposed to combined magazines having a plurality of puncture elements as disclosed in e.g. WO 2011/044971 A1 or WO2012/089524 A1.

As further used herein, a body fluid generally may refer to an arbitrary body fluid of a human or animal user which may be generated by puncturing a skin portion of the user. In the following, preferably, reference will be made to whole blood and/or interstitial fluid. Still, other body fluids are generally feasible.

The sampling element has a housing comprising a chamber with at least one puncture element stored therein. As used herein, a housing generally is an element providing protection against mechanical influences from the outside, such as protection against mechanical shocks. Thus, the housing may provide a full or partial enclosure against the surrounding environment. Further, the housing may provide protection against chemical influences, such as protection against moisture. The housing preferably is at least partially made as a rigid housing, i.e. a housing which is not visibly deformed by forces usually occurring during use of the sampling element, such as forces due to the housing's own gravitational force. Thus, as an example, the housing may fully or partially be made of a plastic material, such as one or more of the plastic materials disclosed in the method described in WO 2012/140027 A1. Thus, as an example, one or more thermoplastic materials may be used.

As further used herein, a chamber generally is an open space contained within the housing which fully or partially is surrounded by the housing. Most preferably, the chamber is fully surrounded by the housing, notwithstanding the fact that the housing may contain one or more openings, such as one or more puncture openings which will be disclosed in further detail below.

As further used herein, a puncture element generally is an element adapted for perforating a skin portion of a user, in order to create one or more openings, punctures or incisions in the skin portion through which the body fluid may be sampled and/or through which the body fluid may leave a body tissue located underneath the skin portion. Thus, generally, the puncture element may be selected from the group consisting of a lancet or lancing element, a needle, a knife, a micro-sampler or a cannula. Most preferably, the puncture element is a needle or a lancet. The lancet may be a flat lancet, a round lancet or a lancet generally having an arbitrary cross-section, such as a polygonal cross-section. Generally, the puncture element may comprise an arbitrary tip for perforating, also referred to as puncturing, a skin portion of the user. The tip, as an example, may be a round needle tip or an acute needle tip.

Preferably, the puncture element comprises a micro-sampler, which is a combined element comprising both a tip for puncturing the skin portion and at least one capillary element for transporting body fluid from the skin portion and/or a tissue portion located underneath the skin portion by capillary forces. As an example and as will be outlined in further detail below, the puncture element may comprise a flat lancet, such as a flat lancet generated by cutting and/or etching from a flat metal disc, with one or more capillary channels on at least one surface of the puncture element, preferably one or more open capillary channels, preferably one or more capillary channels with hydrophilic properties. The one or more open capillary channels may comprise an at least partially opened slit or groove in a surface of the puncture element. The slit or groove may be straight or bent. The slit or groove may at least partially be opened along its longitudinal extension. For further potential embodiments of micro-samplers, reference may be made to one or more of WO 2012/089524 A1 and WO 2012/140027 A1. Still, other embodiments are feasible.

The tip of the puncture element is movable through at least one puncture opening of the housing in order to perforate a skin portion of the user. Thus, as an example, the housing may comprise a puncture opening leading to the chamber, through which the tip of the puncture element is movable when performing a puncturing motion. As an example, the chamber may have an elongated shape, with a longitudinal axis, wherein the puncture element is stored along the longitudinal axis within the chamber and wherein the puncture element may move along the longitudinal axis, in order for the tip and, optionally, further parts of the puncture element, to leave the chamber in order to perforate the skin portion of the user. The chamber preferably may be closed along the walls of the longitudinal axis, and the puncture opening may be at a front face of the chamber.

After perforating the skin portion of the user, the puncture element may be retracted into the chamber and may be restored within the chamber. Within the chamber, the puncture element may be stored in a relaxed state. Alternatively, the puncture element may be stored in a bent state, in order to keep the puncture element in place by deformation, such as e.g. disclosed in WO 2012/140027 A1. Additionally or alternatively, other means for keeping the puncture element in place when stored or restored within the chamber may be present.

The sampling element further comprises at least one compression element. The compression element may at least partially surround the puncture opening, preferably from an outside of the housing outside the chamber, as will be outlined in further detail below. The compression element is adapted to increase a pressure of the body fluid within a body tissue of the user in a region of puncturing when pressed onto the skin portion of the user. This process of forcing body fluid from a puncture opening created by a puncture element is also referred to as milking.

Compression elements, also referred to as compression units, expression elements, expression units, expression rings or compression rings, are generally known in the art. Thus, as an example, compression units are disclosed in EP 1 643 908 B1. Generally, as used herein, a compression element is an arbitrary element adapted for increasing an internal pressure within the body tissue which is fully or partially covered by the skin portion to be perforated by the puncture element, in order to express body fluid out of an incision generated by the puncture element. The internal pressure preferably is created by mechanical forces only, which are exerted by the user pressing the compression element onto the skin portion, as opposed to other stimulation devices using, as an example, heat, ultrasound and or other stimulation techniques. As will be outlined in further detail below, the compression element may comprise a ring-shaped protrusion which may fully or partially surround the puncture opening of the housing and/or which may fully or partially surround the puncture element during a lancing motion and which may be pressed onto the skin portion of the user, by a force exerted by the user himself and/or the analytical device.

As proposed by the present invention, the compression element is movably mounted to the housing. Thus, the compression element and the housing generally are independent elements which may move relative to each other, wherein the compression element is movably mounted to the housing by an arbitrary mounting mechanism. The sampling element provides at least one locking mechanism for releasably locking the compression element in at least two positions, the at least two positions comprising a first position and a second position, the second position being offset from the first position. Thus, the compression element is movably mounted to the housing and is movable when the locking mechanism is released. Thus, generally, the compression element may move at least between the first position and the second position or vice versa when the locking mechanism is released. The second position, as an example, may be a position in which the compression element abuts the housing and, thus, may not move any further. Generally, the first position and the second position may be end positions of a movement. Other embodiments are feasible.

Preferably, the second position may be offset from the first position in a longitudinal direction of the sampling element, wherein, as an example, the longitudinal direction of the sampling element may be defined by a longitudinal extension of the chamber, by an axis of longitudinal extension of the puncture element, a direction of a puncture motion or a combination thereof. Thus, generally, the named directions may be identical.

By movably mounting the compression element to the housing, a position of the compression element, which may take at least two positions, may function as an indication whether the sampling element has been used or not. Thus, when the compression element is pressed onto the skin portion of the user, in a released state, the compression element may be pushed from the first position into the second position, thereby indicating that the sampling element has been used. The user and/or an analytical device using the sampling element may recognize, by eye, by inspection of the sampling element and/or by an arbitrary detector or detection mechanism, whether the compression element is in the first position (indicating an unused state of the sampling element) or in the second position (indicating a used state of the sampling element) and, consequently, automatically or by any action taken by the user, prevent a reuse of an already used sampling element. Thus, as an example, and as will be outlined in further detail below, the analytical device may comprise a mechanical mechanism such as a mechanical lock which automatically prevents a reuse of the sampling element when the compression element is in the second position. As an example, the analytical device may provide a lock and/or a blocking element which automatically prevents bringing a sampling element into an application position in case the compression element is in the second position. Additionally or alternatively, the analytical device may provide a detection mechanism or detection device adapted for detecting whether the compression element is in the first position or in the second position and taking appropriate actions in case the second position is detected, such as giving a warning to a user and/or automatically blocking a further use of the sampling element.

As outlined above, the compression element is movably mounted to the housing. The movable mounting may allow for a motion of the compression element relative to the housing, preferably in the longitudinal direction. As outlined above, the longitudinal direction generally may be a direction of a puncture motion. The puncture motion may comprise a forward motion of the tip of the puncture element in order to perforate the skin portion of the user and, optionally, a backward motion of the tip in order for the puncture element to be restored within the chamber, as disclosed e.g. in one or both of WO 2012/140027 A1 and WO 2012/089524 A1. Thus, the second position may be offset from the first position in a backward direction or direction of the backward motion, which may also be the direction of a pushing force exerted onto the compression element by the skin portion of the user when the compression element is pressed onto the skin portion. Thus, generally, the compression element may be pressed onto the skin portion in a direction perpendicular to a surface of the skin portion, which may be a direction of the forward motion of the tip of the puncture element, and, thereby, the compression element may be pushed in the direction of the backward motion.

Generally, the compression element may be linearly movable with regard to the housing. Preferably, the compression element may be linearly movable parallel to a longitudinal axis of the sampling element.

The compression element may comprise at least one trigger portion adapted to exert a trigger action onto a trigger of an analytical device using the sampling element when the compression element is moved from the first position into the second position. As used herein, a trigger portion generally refers to a part of the compression element which provides at least one leading edge or surface adapted for exerting the trigger action when the compression element is moved from the first position into the second position. As an example, the trigger portion may provide a rear face or rear surface, having at least one surface component facing into a rearward direction, adapted for providing a trigger force onto the trigger when the rear face or rear surface when the compression element is moved from the first position into the second position.

Thus, as an example, the analytical device using the sampling element may be adapted to automatically trigger the puncture motion when the compression element is pushed from the first position into the second position. For this purpose, as will be outlined in further detail below, the analytical device may comprise at least one trigger mechanism adapted to trigger a lancing drive or puncture drive to drive the puncture motion, wherein the trigger mechanism is adapted to be actuated by the compression element when the compression element is moved from the first position into the second position. As an example, the trigger portion of the compression element may comprise an edge of the compression element, preferably an edge or surface of a mounting portion of the compression element by which the compression element is mounted to the housing, and, more preferably, an edge or surface of at least one mounting arm of the compression element. When the compression element is moved from the first position into the second position, the edge of the compression element may engage the trigger mechanism of the analytical device, which, as an example, may comprise a switch and/or a rocker, thereby triggering and/or releasing a puncture drive, also referred to as a lancing drive, and/or a coupling element to drive the puncture motion. Trigger elements of this kind are generally known to the skilled person and known in the art, such as from WO 2011/044971 A2 and/or from EP 1 669 028 A1. Trigger mechanisms of this or similar kind may also be implemented within the present invention, in combination with the idea of using the compression element for triggering a trigger of an analytical device.

As outlined above, the compression element is movably mounted to the housing. Preferably, the compression element is movably mounted to the housing such that, when the locking mechanism is released and when the compression element is pressed onto the skin portion of the user, the compression element is moved from the first position into the second position. Most preferably, the movement of the compression element is a linear movement.

As outlined above, the compression element generally is adapted to increase a pressure of the body fluid within a body tissue of the user in a region of puncturing when pressed onto the skin portion of the user. Thus, the region of puncturing may fully or partially be surrounded by the compression element when the compression element is pressed onto the skin portion. Specifically, the compression element may comprise an annular compression element portion. Thus, the compression element may comprise one or more compression rings having an annular protrusion, which at least partially surrounds the puncture opening of the housing and which is adapted to be pressed onto the skin portion in the region of puncturing. The compression element may further have a mounting portion movably mounted to the housing. The mounting may take place such that, in any position of the compression element, the compression ring is located on a side of the housing facing the skin portion. The at least two positions of the compression element may simply differ with regard to a distance between the compression element and the housing.

As outlined above, the compression element may be mounted in a movable fashion to the housing by one or more mounting portions. Thus, as an example, the at least one mounting portion may comprise at least one mounting arm, preferably at least two mounting arms and, most preferably, precisely two mounting arms, which is or are slidably guided in one or more guidings of the housing. Thus, as an example, the guiding may comprise one or more guide rails, such as a pair of guide rails, preferably at least two guide grooves. These guide grooves, however, preferably leave some clearance to allow an analytical device to take over the guiding of the compression element when in use, as will be discussed in more detail below.

The at least one mounting arm preferably may be or may comprise at least one spring arm and/or may have elastic and/or flexible properties. Thus, the at least one mounting arm may fully or partially be designed as one or more flexible or elastic plastic arms extending in a rearward direction from a body of the compression element, wherein the body of the compression element preferably comprises the at least one annular protrusion facing in a forward direction.

The at least one mounting arm, preferably the pair of mounting arms, preferably may be or may comprise one or more snap arms adapted to snap into at least one corresponding notch in the first position and the second position. Thus, the at least one mounting portion may comprise a pair of snap arms which, as an example, may be guided in a pair of guide rails within the housing, which each are adapted to snap into one or more notches in the first position and the second position. Thus, for each snap arm, a first notch may be provided in the first position and a second notch in the second position.

The housing, as discussed above, may fully or partially surround the chamber. The housing may be made of one piece or may be made of two or more pieces. Thus, as an example, the housing may be composed of a bottom part and a cover part.

As outlined above, the housing may comprise at least one guiding, preferably at least one guide rail, wherein the compression element slidably is mounted into the guiding. Thus, as outlined above, the compression element may comprise one or two mounting arms, preferably one or two snap arms, which are movably or slidably mounted in the at least one guide rail. The guiding preferably may extend along a longitudinal axis of the sampling element. Thus, as an example, the at least one guide rail, which may be a slot-type guide rail or, more preferably, a pair of slot-type guide rails within the housing, preferably may extend parallel to a longitudinal axis of the sampling element.

As outlined above, the locking mechanism is adapted for releasably locking the compression element in the at least two positions. As an example, the locking mechanism may comprise a releasable snap-fit connection. As used herein, a snap-fit connection is a connection comprising at least two connection elements interact by a form-fit connection. Thus, as an example, the snap-fit connection may use elastic properties of at least one of the connection elements. Thus, at least one of the connection elements temporarily, during locking, may deform elastically, in order to, subsequently, engage the other connection element. As an example, the snap-fit connection may comprise at least one snap hook and at least one catch, wherein the snap hook, after appropriate elastic deformation, may engage with the catch. As an example, the compression element may comprise the snap hook, such as by providing one, two or more snap arms, and the housing may provide the at least one catch, such as by providing two or more appropriate notches for engaging with the snap hook.

Thus, as outlined above, the compression element, preferably the at least one mounting arm, may comprise at least one snap arm which is adapted to releasably snap into a first notch when the compression element is in the first position and into a second notch when the compression element is in the second position. Thus, the at least one mounting arm generally may be designed as at least one snap arm. The snap arm, as outlined above, preferably provides flexible or elastic properties. Other options are generally feasible.

As outlined above, the sampling element preferably is a disposable sampling element adapted for single use. Thus, the first position of the compression element may be an unused position and the second position may be a used position. Preferably, the sampling element may contain precisely one puncture element and, thus, may be a disposable sampling element adapted for single use. An appropriate analytical device may be adapted for recognizing whether the compression element is in the first, unused position or in the second, used position.

Thus, as an example, at least a part of the compression element may protrude from the housing and may form a protrusion from the sampling element when the compression element is in the second position. This protrusion may be indicative of the sampling element being used. Thus, an analytical device using the sampling element may recognize the protrusion and, thus, may recognize that the compression element is in the second position and, thus, is used. Consequently, the analytical device may be adapted to perform several actions, such as preventing the sampling element from being used again, in case the protrusion is recognized and/or blocking a puncture actuator and/or a coupling element in order to block a puncture motion. Other options are feasible, such as a combination of the named options and/or a display of information to a user indicating that the sampling element has already been used. Further, the analytical device may be adapted to mechanically prevent a used sampling element from being brought into an application position such as by providing one or more abutment portions abutting the protrusion. As an example, the at least one protrusion may be formed by one or more of the mounting elements, such as by one or more of the snap arms. The protrusion, specifically, may also provide the above-mentioned edge or surface of a mounting arm of the compression element, which, simultaneously, may be used for triggering a trigger mechanism.

As outlined above, the puncture element generally may be or may comprise an arbitrary type of lancet or lancing element. Further, the puncture element may comprise additional elements, such as one or more elements for transporting and/or transferring a sample of the body fluid. Thus, as an example, the puncture element may comprise at least one capillary, also referred to as a capillary element, adapted to receive body fluid from the region of puncturing. The at least one capillary may start immediately at the tip of the puncture element or may be offset from the tip of the puncture element. Thus, as an example, the at least one capillary may start at a distance of 0.3 to 2 mm from the tip of the puncture element. Other embodiments are feasible. The capillary element preferably may extend along a longitudinal axis of the puncture element. The capillary, as an example, may be adapted to receive body fluid from the region of puncturing, wherein the body fluid received within the capillary fully or partially forms the sample of the body fluid. Thus, when referring to a sample of the body fluid, reference may be made to the whole body fluid received by the sampling element or to a part thereof. The capillary may be adapted to receive the body fluid and, optionally, may be adapted to transfer the body fluid onto another part of the sampling element and/or the analytical device, such as onto a test field and/or a test chemical contained within the sampling element and/or contained within the analytical device. As an example, the puncture element may be or may comprise a micro-sampler having at least one capillary slot. The capillary slot preferably may be located on a surface of the puncture element. Thus, as an example, the puncture element may be a flat micro-sampler which may be produced by embossing and/or etching a flat disc. The sampling element may be adapted to lead the at least one capillary slot close to an optional test field of the sampling element when the puncture element is retracted into the chamber, thereby allowing for a transfer of the sample of the body fluid onto the test field. Further optional details will be given below.

As outlined above, the sampling element may be a sampling element for puncturing purposes only. Thus, the sampling element may be a pure puncture aid, without any further functions, preferably a single-puncture element sampling element for single use. Alternatively, the sampling element may comprise additional functions, such as at least one detection function. Thus, preferably, the sampling element may be a combined sampling element, providing both puncture function and analytical function.

Thus, as an example, the sampling element may further comprise at least one test chemical adapted for performing at least one detectable detection reaction in the presence of at least one analyte to be detected. The sampling element, as outlined above, may be adapted to transfer body fluid onto the test chemical, such as by transferring a body fluid from the puncture element, preferably the microsampler, onto the test chemical, more preferably onto a test field comprising the at least one test chemical.

Generally, as used herein, a test chemical is a chemical substance and/or a mixture of chemical substances adapted for performing at least one detectable detection reaction when the analyte is present. As an example, the detection reaction may be an electrically detectable and/or an optically detectable detection reaction. In the following, reference will be made to optical detection reactions which is the preferred option within the present invention. Generally, the test chemical may be or may comprise an arbitrary substance or mixture of substances adapted for performing the at least one detection reaction. For potential test chemicals, also referred to as test chemistries and/or detector chemicals and/or detector substances, reference may be made to the prior art. Thus, as an example, reference may be made to WO 2012/140027 A1 and the test chemicals disclosed therein, which may also be used within the present invention. Thus, preferably, the test chemical is a test chemical stable against environmental influences, preferably stable against humidity, as defined in WO 2012/140027 A1. Still, other test chemicals may be used.

Most preferably, the at least one test chemical includes at least one enzyme adapted to perform at least one enzymatic reaction in the presence of the analyte to be detected. As an example, in case glucose is to be detected, the enzyme may comprise glucose oxidase and/or glucose dehydrogenase. Further, the at least one test chemical may comprise one or more mediators and/or one or more co-enzymes. Further, the at least one test chemical may comprise one or more dyes, which, when the analyte is present and when the detection reaction takes place, are adapted for performing a color change and/or another type of optically detectable change, such as a change in fluorescence properties.

For performing a transfer of the body fluid onto the test chemical, several techniques are feasible. Thus, as outlined above, the test chemical may be located close to the puncture element when the puncture element is stored within the chamber. As an example, the puncture element, after performing the puncture motion, may be guided by an appropriate internal guiding structure of the chamber, such that the puncture element and/or a part thereof, such as the at least one capillary, are guided close to the at least one test chemical such as close to at least one test field comprising the at least one test chemical. For potential details of this option, reference may be made to one or both of WO 2012/089524 A1 and WO 2012/140027 A1. Additionally or alternatively, the puncture element may be pressed onto the test chemical and/or the test field. Various other types of sample transfer are known.

As outlined above, the test chemical preferably may be contained in at least one test field. As used herein, a test field generally refers to a coherent amount of the test chemical forming one or more layers, the test field preferably having at least one test field surface and/or application surface. In addition to one or more layers containing the at least one test chemical, the test field may comprise additional elements, such as one or more additional layers. Thus, as an example, the test field may comprise at least one test chemical layer comprising the at least one test chemical and, preferably, one or more additional layers, such as one or more separation layers for separating off unwanted parts of the sample of the body fluid, such as red blood cells, and/or one or more layers having reflecting properties, such as one or more pigment layers providing a bright, preferably a white, background for measurement. Thus, the test field may comprise a multi-layer setup with at least one test-chemical layer and at least one cover layer, such as at least one separation layer and/or at least one pigment layer, covering the at least one test chemical layer. The test field surface may be a surface of the at least one cover layer, such that the sample of the body fluid is applied to the at least one cover layer and has to penetrate the at least one cover layer before reaching the at least one test chemical layer. Still, other layer setups are feasible, such as single-layer setups containing the test chemical layer, only.

Most preferably, the test chemical is accessible from the chamber. Thus, the test field may be accessible from the chamber. As an example, one or more walls of the chamber may provide one or more windows, i.e. one or more openings, which fully or partially are covered by the test field such that the test field is fully or partially accessible from an interior of the chamber. Consequently, the test field and/or a part thereof may form a part of at least one wall of the chamber, such that sample fluid transferred into the chamber by the puncture element may be transferred from the puncture element onto the test field inside the chamber. Thus, the sampling element may be adapted to take up the sample of the body fluid with puncture element in a puncture motion of the puncture element and to transfer the sample of the body fluid from the puncture element onto the test chemical, such as by approximating the puncture element to the test field containing the test chemical, preferably within the chamber. Consequently, the sampling element may be adapted to bring the puncture element close to the test chemical when the puncture element is pulled back into the chamber, such as in a rearward motion of the puncture element, after the puncture motion and/or as a part of the puncture motion. As outlined above, the chamber walls may provide an appropriate guiding structure for the puncture element, in order to lead the puncture element close to the test chemical, preferably close to the test field.

The housing, as outlined above, may comprise one or more openings, such as the puncture opening. The housing may further comprise at least one actuator opening adapted for a coupling element to enter the chamber and to engage with the puncture element in order to drive the puncture element for a puncture motion. The coupling element specifically may be part of a puncture actuator and/or may be coupled to a puncture drive or lancing drive of an analytical device. The coupling element may move in one or more dimensions, such as in a longitudinal direction and, optionally, in one or more directions perpendicular to the longitudinal direction. Thus, the coupling element may be a z-actuator, an xz-, a yz- or an xyz-actuator. Additionally or alternatively, however, the coupling element may be adapted to rotate or pivot around at least one axis, such as an axis perpendicular to the longitudinal direction. The analytical device may comprise one or more puncture drives, also referred to as a lancing drive which may permanently or releasably be coupled to the coupling element for driving a puncture motion. The at least one puncture drive may comprise an arbitrary driving mechanism for driving a puncture motion or lancing motion, such as one or more spring mechanisms generally known in the art.

As an example, the at least one actuator opening may be located at an end of the housing opposing the end of the housing containing the puncture opening. Generally, as used herein, a coupling element is an arbitrary element or actuator which is adapted for driving the puncture element to perform a puncture motion. As an example, the coupling element may comprise one or more movable hooks and/or one or more movable ramps. Potential embodiments of the coupling element, reference may be made to one or more of the above-mentioned prior art documents, such as WO 2011/044971 A2 and/or WO 2012/089524 A1. Still, other embodiments are feasible.

The coupling element, as outlined above, may be connected to, may be connectable to or may be part of at least one drive element of the analytical device. The at least one optional drive element and the at least one coupling element, in conjunction, may form a puncture actuator of the analytical device. Generally, as used herein, a drive element refers to an arbitrary actuator adapted for driving the puncture element to perform the puncture motion. The drive element generally may comprise an arbitrary driving mechanism, such as one or more of the driving mechanism is disclosed in WO 2011/044971 A2 and/or WO 2012/089524 A1.

The coupling element may engage with the puncture element in the generally arbitrary fashion in order to drive the puncture element for a puncture motion. Thus, the coupling element may simply push the puncture element in a forward motion. Additionally or alternatively, the coupling element may also be adapted for pulling back the puncture element after the puncture motion, i.e. after a forward motion of the puncture element, in order to perform a rearward motion and/or in order to re-store the puncture element within the chamber. Thus, as an example, the puncture element may comprise one or more hooks which may be adapted to engage with one or more openings of the puncture element.

The puncture element may comprise at least one connection element adapted to engage with the at least one coupling element for being driven to perform the puncture motion. Thus, as an example, the at least one connection element, as outlined above, may comprise one or more openings within the coupling element, preferably at a rearward end of the puncture element opposing the tip of the puncture element. Thus, the connection element may comprise at least one opening adapted to be engaged by the coupling element, e.g. a hook of the coupling element.

The sampling element, as an example, may have a total volume of less than 3 cm$^3$, preferably a total volume of 0.5 to 2 cm$^3$. As an example, the sampling element may have a length of 3 mm to 30 mm, preferably a length of 5 mm to 20 mm, and may have a width and/or height of 2 mm to 20 mm. The sampling element may have a circular and/or square cross-section in a plane perpendicular to a longitudinal axis of extension. Other embodiments are feasible.

The compression element preferably may have a contact area which, during compression, gets in contact with a skin of the user. The contact area, as an example, may be a surface area of the annular protrusion. Thus, as an example, the contact area may be an annular or circular area. As an example, the contact area may be a ring-shaped area having a ring with (i.e. a difference between an outer radius and an inner radius) of 0.2 to 3 mm, preferably 0.3 to 2 mm and more preferably 0.5 to 1 mm. The contact area, as an example, may be in the range of 0.5 to 30 mm$^2$, preferably in the range of 1 mm$^2$ to 20 mm$^2$. Other embodiments are feasible. The annular protrusion, as an example, may have a diameter of 2 to 10 mm, preferably a diameter of 3 mm to 5 mm.

The compression element may be adapted to actuate a trigger of an analytical device using the sampling element. Typically, the compression element may be pressed onto the skin of the user by forces of more than 1 N, such as forces of 2 to 30 N, 3 to 15 N or 5 to 10 N. The trigger may be adapted such that an actuation by the compression element with trigger forces of more than 1 N may lead to a trigger action. Thus, the trigger may be adapted to initiate a puncture motion once a trigger force exceeding a trigger threshold is exerted onto the trigger by the compression element. The trigger force may be in the range of 0.5 N to 10 N or 1 N to 10 N. Other embodiments are feasible.

The compression element preferably may fully or partially be made of a material which is break-proof, at least under typical forces occurring during normal use, such as forces up to 20 N, preferably up to 30 N. Further, the compression element may fully or partially be made of a flexible and/or elastic material. Specifically, the compression element may comprise a mounting portion, specifically a mounting portion having at least one mounting arm. The mounting portion, specifically the at least one mounting arm, preferably may fully or partially be made of at least one flexible and/or elastic material. As an example, at least one plastic material may be used, such as at least one thermoplastic material. As an example, one or more of the following materials may be used: a polycarbonate (PC); a polyester (PE); an acrylonitrile butadiene styrene (ABS); a cyclo olefin copolymer (COC); a poly(methyl methacrylate) (PMMA); a polystyrene (PS); a polyethylene terephthalate (such as PET, PETE, PETP or PET-P). Further, other materials and/or combinations of two or more of the named materials and/or combinations of one or more of the named materials with one or more other materials may be used. Specifically, the compression element, more preferably the protrusion, may fully or partially be made of a skin-compatible or skin-tolerant material, preferably a material which is not prone to provoke allergies.

The at least one mounting arm may, as a whole or as a part, be part of the locking mechanism. Thus, as an example, a rear end of the mounting arm may be bent in order to release the locking mechanism.

As outlined above, the sampling element preferably is a single sampling element, i.e. a sampling element which contains precisely one puncture element. Thus, the housing may contain precisely one chamber with the precisely one puncture element located therein. Preferably, the sampling element may be a disposable single-use sampling element. The sampling element, preferably the single sampling element, may be packaged, such as by using commonly known packaging technologies. Thus, as an example, a single sampling element may be packaged in a compartment of a packaging. As an example for commonly known packaging technologies, use may be made of one or more of vials, blister packs or packaging strips such as tablets strips. Other packaging technologies are feasible. As an example, single sampling elements may be packaged in a loose fashion, such as one by one, in respective compartments of blister packs or vials. An advantage of the present invention, with the compression element being an element separate from the housing, resides in the fact that the sampling elements may be packaged such that the single sampling elements and/or their chambers may be sealed individually and, thus, may be protected against detrimental effects of moisture and/or air. Thus, as an outer packaging, simple cardboard packages or other packages without sophisticated protective properties against moisture and/or air may be used.

Still, in a further aspect, an analytical magazine is disclosed having a magazine housing and having a plurality of sampling elements as proposed within the present invention stored therein. Preferably, the sampling elements are stored independently from each other within the analytical magazine, i.e. without mechanical connection and/or without being combined by a common housing. Thus, the sampling elements preferably are stored and may be handled independently from each other.

In a further aspect of the present invention, an analytical device is disclosed, the analytical device being adapted for using the sampling element according to the present invention, such as the sampling element according to one or more of the above-mentioned embodiments and/or the sampling element according to one or more of the embodiments disclosed in further detail below. The analytical device comprises at least one coupling element adapted for driving the puncture element to perform a puncture motion. Further, as outlined above, the analytical device may comprise at least one driving element which may fully or partially be connected or connectable to the coupling element. As outlined above, the driving element and the coupling element, in conjunction, may form a puncture actuator adapted for driving the puncture element to perform a puncture motion. The driving element also may be referred to as the lancing drive or the puncture drive. With regard to potential definitions and embodiments of the coupling element, the driving element and the puncture actuator, reference may be made to the disclosure given above. Further, reference may be made to the coupling elements, drive elements and puncture actuators as disclosed in one or more of the above-mentioned prior art documents, such as in WO 2011/044971 A1 and/or WO 2012/089524 A1. Thus, generally, the analytical device may comprise one or more release elements and, optionally, one or more release drive elements driving the one or more release elements. The at least one release element and the at least one optional release drive element, in conjunction, may form at least one release actuator.

The at least one coupling element may be driven by an arbitrary drive element contained within the analytical device, such as by a motor and/or a rotor and/or a spring element contained within the analytical device. Thus, for driving the coupling element, the drive element may comprise one or more of a motor, such as an electrical motor, a spring element, such as a coil spring and/or another type of spring element, a mechanical and/or electrical energy storage adapted for providing energy to be transformed into the puncture motion.

The analytical device further comprises at least one release element, the release element being adapted for releasing the locking mechanism of the sampling element in the first position before performing the puncture motion in order to allow for the compression element of the sampling element to be moved from the first position into the second position. Thus, generally, a release element, as used herein, is an arbitrary element or an arbitrary combination of elements adapted for releasing the above-mentioned locking mechanism. In a most simple case, as will be outlined in further detail below, the release element may comprise one or more bars, also referred to as release bars, which may be pushed in between the compression element and the housing of the sampling element, such as in between a mounting arm, more preferably a snap arm, of the compression element and the housing, in order to release the mounting element from the housing. Thus, as an example, a hook contained in the snap arm may be lifted from a notch within the housing, in order to allow for the compression element to be moved relative to the housing. Most preferably, during moving the compression element, the housing is kept in a fixed position by the analytical device and, thus, does not move with regard to the analytical device. Therefore, the housing preferably leaves enough clearance for the compression element to hand over the guiding of the compression element to structures of the analytical device. This preferred embodiment allows the compression element to be moved by force, such as a force exerted by the compression element onto the skin of the user, without disturbing the position of the housing within the analytical device.

As outlined above, the coupling element may comprise at least one hook adapted to engage with an opening of the puncture element of the sampling element. Still, other types of coupling elements are feasible, as discussed above.

As outlined above, the release element may comprise at least one release element bar adapted to be pushed in between at least a part of the compression element and the housing of the sampling element in order to release the locking mechanism. As an example, the at least one release element bar may comprise a wedge which may be forced in between the compression element and the housing, such as in between at least one mounting portion of the compression element and, more preferably, in between a snap arm of the compression element and the housing, in order to release the locking mechanism. The wedge, as an example, may be located at a free end of the release element bar. Preferably, at least two release element bars are comprised, each comprising a wedge at its free end facing towards the sampling element.

The coupling element and the release element may be driven independently or, preferably, may be driven by a link mechanism. As used herein, a link mechanism generally refers to a mechanism which is adapted to fully or partially couple the motions of the coupling element and the release element. The link mechanism thus may comprise one or more arbitrary elements adapted to couple these motions. The coupling of the motions by the link mechanism may comprise a coupling in the same direction of motion or in different directions. Further, the link mechanism may comprise a differential and/or may comprise a gear drive having a fixed or variable gear transmission ratio. The coupling element and the release element may further be driven by a combined actuator or drive or, preferably, by independent actuators or drives. Thus, as outlined above, the coupling element may be driven by at least one drive element, and the release element may be driven by at least one release drive element. These drive elements each may comprise an arbitrary type of actuator, as outlined above with regard to the drive element of the coupling element. The drive element of the coupling element and the release element and the link mechanism, in conjunction, may form a common drive of the coupling element and the release element.

The process of using the sampling element may comprise at least two phases, a preparation phase and a lancing and/or sampling phase. During the preparation phase, the coupling element may engage the lancing element and, preferably at least partially simultaneously, the release element may release the locking mechanism, thereby releasing the compression element from the housing of the sampling element. This movement preferably may be relatively slow, such as some millimeters per second up to some centimeters per second. During the lancing phase, the puncture element may be moved relatively fast, such as in the order of one or more meters per second. This can be performed by two individual actors, i.e. the drive element and the release drive element, which may specialized to their tasks and may act separately on the coupling element and the release element. Alternatively, as outlined above, a combination of these actuators is also possible. As known from EP 1 669 028 and WO 2011/044971 A2, however, especially the drive element of the coupling element can do a preparation stroke as well as a lancing stroke. This combination, however, may lead to a drive with relatively long movement distances and, thus, may lead to large steering curves with the inherent friction issues. Alternatively, the release drive element, which may also be referred to as the preparation drive, can move the entire lancing drive forward and backward to do the preparation movement of the coupling element which afterwards does the lancing stroke at high velocity. This typically means to provide the space not only of the lancing drive but also for moving it around. Additionally these combined drives may become the more restricted in fitting into a small device the more tasks they have to do. Thus, generally, various possibilities of driving the release element and the coupling element are possible and may be realized within the present invention.

Still, as outlined above, the analytical device preferably comprises at least two actuators which, preferably, independently may drive the coupling element and the release element. Thus, the analytical device may comprise at least one drive element for driving the coupling element and may comprise at least one release drive element for driving the release element. These drive elements preferably are specialized drives elements and, preferably, may act independently. The drive elements may act on the link mechanism which leads their motions to the coupling element and, specifically in case of the preparation phase, to the coupling element and the release element as well. The drive elements in conjunction with the link mechanism may act in the fashion of an inversely operating differential drive known from automotive technology. Still, the link mechanism may provide limited linear motions, preferably in a sequential fashion, rather than continuous rotation of motions as known in automotive differential drives.

The drives, i.e. the drive element and the release drive element, each independently may comprise one or more of:

one or more motors, one or more spring elements, one or more gears or similar elements which generally are well known to one skilled in the art.

Figure 4:
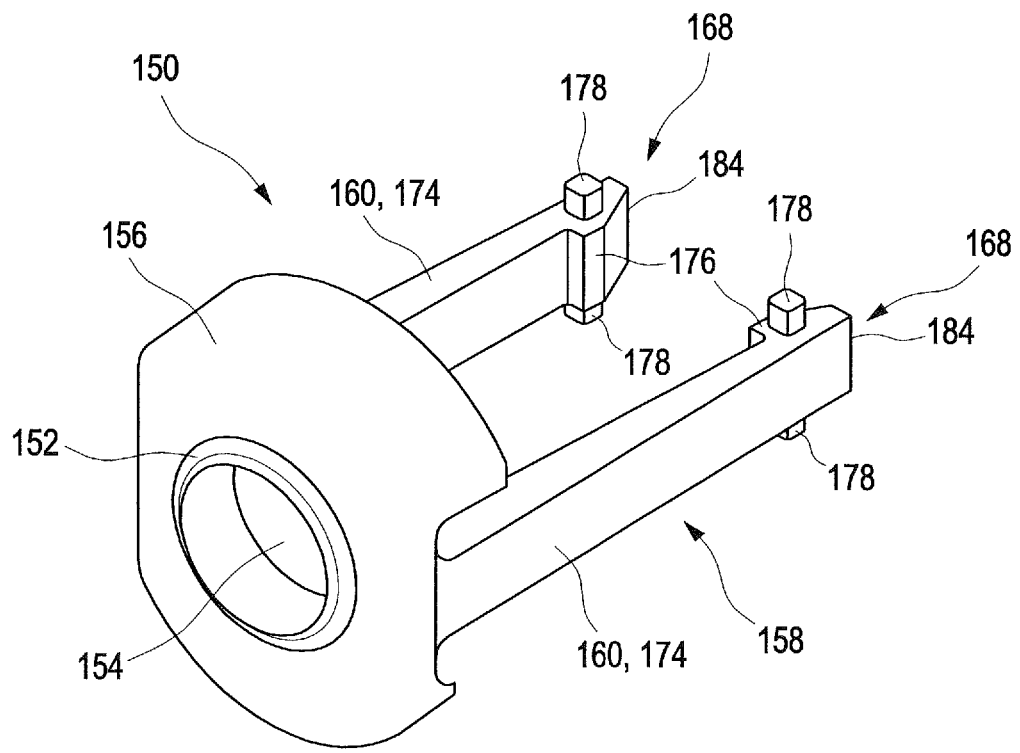

The drives, i.e. the drive element for driving the coupling element and the release drive element for driving the release element, may act entirely independently from each other. As outlined above, however, it also is possible to connect these drives. For instance, the release drive element, which may also be referred to as the drive for the preparation phase, may be or may comprise a simple push button which also may act as a cocking means for the lancing drive as e.g. is described in EP 1 384 438 B1 (FIG. 4). While doing the forward movement of the release element and the coupling element it may tension, e.g. by means of rack and pinion, the drive spring which later drives the lancing motion. Additionally or alternatively, the preparation movement may be performed by rotating the cocking element while the puncture motion may be driven by a spring-driven lancing element, such as in EP 1 669 028 A1.

As outlined above, the analytical device may comprise a link mechanism for driving the coupling element and the release element. The link mechanism may comprise at least one lever directly or indirectly connected both to the coupling element and to the release element. As an example, the lever may comprise one, two or more rotational axes. In case a plurality of rotational axes, such as two rotational axes, are used, the rotational axes may be used alternatively. Thus, as an example, the lever may comprise a rotational axis, wherein the drive element and/or the coupling element may be connected to the lever on a first arm with regard to the rotational axis, and wherein the release element and/or the release drive element may be connected to the lever on a second, opposing arm of the lever, such that the rotational axis is located in between the connection of the coupling element and the connection of the release actuator. A distance between the rotational axis and a connection point of the drive element and/or the coupling element, respectively, and a distance between the rotational axis and a connection point of the release element and/or the release drive element, respectively, may determine the respective transmission ratios or gear ratios of the lever, which, by adjusting these distances, may be adjusted. Further, the stroke of the respective actuators may be adjusted by these distances.

The coupling element and the release element may be mounted independently. Still, preferably, the release element and the coupling element may be mounted on a common mounting. Thus, the coupling element and the release element may be mounted on a common guide, such as a linear guide. Thus, as an example, the guide may comprise one or more slides and/or one or more slide rails or slide bars on which the release element may be mounted, in order to perform a linear motion, preferably in the direction of the puncture motion. Preferably, the coupling element and the release element may be mounted on the common guide and may be movable independently on this guide.

The release element, in one embodiment, may be spring-biased, preferably in order to reengage the locking mechanism and to disengage the coupling element form the puncture element after the puncture motion, such as the lancing or sampling action, has taken place. Thus, as an example, the release element may perform a forward motion, such as a forward motion driven by the preparation drive, in order to release the locking mechanism. Thus, as outlined above, a wedge contained in the release element may be pushed in between a part of the compression element and the housing, in order to release the locking mechanism, such as in order to release one, two or more snap arms. As outlined above, during triggering of the puncture motion and/or during use of the sampling element, the compression element may move from the first position to the second position. During that movement, the release element may be kept in position in order to keep the locking mechanism unlocked or released, at least until the compression element has reached the second position. The spring-biasing may comprise at least one spring element adapted to pull or push the release element in a backward direction. The release element may be held in a forward position until the lancing has taken place and then may be allowed to retract.

As discussed above, the analytical device may further comprise at least one trigger mechanism adapted to trigger a puncture motion of the puncture element. Thus, the trigger mechanism may be adapted to trigger a lancing drive acting directly or indirectly onto the puncture element. The trigger mechanism may be adapted to be actuated by the compression element, when the compression element is moved from the first position into the second position. A compression force may be provided by the trigger mechanism and may be transmitted to the skin by the compression element. Thus, as discussed above, the trigger mechanism may be triggered by a trigger portion of the compression element, such as an edge of the compression element, preferably an edge of a mounting portion of the compression element and, more preferably, an edge of at least one mounting arm of the compression element, such as an edge of a snap arm. Most preferably, the edge is a rearward-facing edge, i.e. an edge facing in a direction opposing a forward motion of the tip of the puncture element. Thus, the forward direction may be a direction towards the skin portion of the user, whereas a rearward direction may be a direction away from the skin portion of the user. As an example, the trigger mechanism, as outlined above, may comprise a rocker and/or push button which, again, may act on the drive element and/or the coupling element, in order to release a forward motion of the puncture element. These types of trigger mechanisms are generally known in the art. Within the present invention, the trigger mechanism may be triggered by the compression element, preferably by a rearward motion of the compression element.

As outlined above, the position of the compression element may be used for detecting whether the sampling element has already been used or not. Thus, in a simple fashion, a protection against reuse may be provided in a rather simple fashion, simply by detecting the position of the compression element. Thus, as an example, the analytical device may be adapted to prevent the coupling element and/or the drive element to drive the puncture motion when the compression element is found to be in the second position, thereby preventing a reuse of a used sampling element, i.e. a reuse of the sampling element in case the sampling is found to be a used sampling element. The preventing of the drive element to drive the puncture motion may take place in various ways. Thus, as outlined above, the drive element itself may be blocked and/or the release drive element may be blocked so that the coupling element may not engage with the puncture element.

Additionally or alternatively, other types of protection against reuse may be implemented. Thus, as an example, the analytical device may be adapted to prevent the sampling element to be located in an application position of the analytical device when the compression element is found to be in the second position, thereby preventing a reuse of a used sampling element, i.e. preventing a reuse of the sampling element in case the sampling element is found to be a used sampling element. As used herein, an application position generally is a position of the analytical device in which a sampling element may be held and a puncture motion may be driven by the analytical device. The analytical device may provide one or more application positions. As an example, the analytical device may provide a housing with a predetermined space contained therein adapted for receiving one or more sampling elements, wherein a puncture motion and, thus, a sampling of the body fluid, may take place when the sampling element is in the application position. The analytical device may provide one or more means transferring one or more sampling elements into the application position, such as one or more transporting means. Thus, as an example, the analytical device may make use of one or more analytical magazines as disclosed above, preferably one or more analytical magazines having sampling elements stored therein which may be handled independently from each other. The analytical device may be adapted such that the sampling elements, one after the other, may be transferred into the application position. The analytical device may provide a simple blocking mechanism adapted for blocking a sampling element to be brought or transferred into the application position in case the compression element is found to be in the second position. Thus, as an example, as discussed above, at least a part of the compression element may protrude from the housing and may form a protrusion from the sampling element when the compression element is in the second position. The blocking mechanism of the analytical device may be adapted to abut the protrusion, thereby preventing the used sampling element to be transferred into the application position. Thus, as an example, the blocking mechanism may be shaped like a fish trap or a weir, in order to abut the at least one protrusion, thereby preventing a used sampling element to be transferred into the application position, whereas, in case no protrusion is present, the blocking mechanism allows for the sampling element (which, in this case, is an unused sampling element) to be transferred into the application position.

The analytical device may further comprise at least one sampling element according to the present invention, such as according to one or more of the embodiments disclosed above and/or according to one or more of the embodiments disclosed in further detail below. As an example, the analytical device may comprise a plurality of the sampling elements. Preferably, the analytical device may be adapted to transfer the sampling elements, one after the other, into an application position of the analytical device, in which the sampling may take place. Thus, as an example, the analytical device may comprise one or more analytical magazines as disclosed above, such as according to one or more of the embodiments disclosed above and/or according to one or more of the embodiments disclosed in further detail below.

Preferably, the analytical device may be adapted to subsequently move or transfer sampling elements into the application position and to perform a puncture motion by using the sampling element in the application position.

As outlined above, the at least one sampling element may be a pure puncturing sampling element, i.e. a sampling element having the puncture element only, without any further detection element. Alternatively and more preferably, the sampling element is a combined sampling element, which, besides puncturing the skin portion of the user, provides one or more additional analytical functions and/or one or more additional analytical aids. Thus, as an example and as discussed above, the at least one sampling element further may comprise at least one test chemical adapted for performing at least one detectable detection reaction in the present of at least one analyte to be detected. As an example, the test chemical may be an optical test chemical adapted for performing at least one optically detectable detection reaction in the presence of the least one analyte to be detected, such as a detection reaction implying a change of a color and/or implying a change of fluorescence or reflective properties of the test chemical. The at least one property may be an indication of a progress of the detection reaction and, thus, may be an indication of a quantity of the analyte within the sample, such as a concentration of the analyte.

Consequently, the analytical device may further comprise at least one detector adapted to detect at least one detection reaction of a test chemical contained within the sampling element. Above, the detector preferably may be or may comprise an optical detector adapted to detect an optically detectable detection reaction of the test chemical. Thus, as an example, the optical detector may comprise at least one light source adapted to illuminate the test chemical of the sampling element, such as to illuminate at least one test field containing the at least one test chemical. Additionally or alternatively, the detector may comprise at least one light-sensitive element adapted to detect light propagating from the test chemical to the detector. The light propagating from the test chemical to the detector may be light emitted by the test chemical, such as fluorescence light and/or phosphorescence light, and/or may be light which is reflected and/or diffused by the test chemical. Thus, as an example, the detector may be adapted to perform a reflection measurement or reflective measurement, in order to determine a remission property of at least one test field containing the at least one test chemical. Thus, the light source may be adapted to illuminate the at least one test field, and the light-sensitive element may be adapted to detect light reflected and/or remitted by the test field. The light-sensitive element generally may be an arbitrary element adapted to detect light and to generate an electrical signal indicating an intensity of the light. Thus, as an example, the light-sensitive element may be or may comprise a photodiode, a photo sensor, a solar cell and/or a combination thereof.

In order to perform an optical measurement, as outlined above, the housing of the sampling element may comprise one or more detection openings, such as one or more windows through which the test chemical, preferably the test field, may be monitored by the detector. Thus, as an example, the housing may comprise a front face having the puncture opening, may comprise a rear face opposing the front face, the rear face preferably having the actuator opening, and, additionally, side faces on longitudinal sides of the housing, one or more of the side faces having the at least one detector opening. Within the chamber, the detector opening may fully or partially be covered by the test field. Thus, the test field may be applied to one or more carrier elements, or preferably a transparent carrier element, wherein the carrier element, from an interior side of the chamber, is applied to the detection opening. Through the detection opening and through the carrier element, the above-mentioned optical detection of the detection reaction may take place.

Further preferred embodiments refer to the above-mentioned use of the analytical device. Thus, the analytical device may be adapted to perform the following steps, preferably in the given order. Still, other orders of the steps are feasible. Further, it is possible to perform two or more of the steps simultaneously or in an overlapping fashion. Further, it is also possible to perform one, two or more of the steps repeatedly. Further, additional steps may be comprised which are not mentioned in the following. The steps are as follows:

a) releasing the locking mechanism by using the release element;
b) driving the puncture element to perform a puncture motion by using the coupling element, thereby generating the sample of the body fluid
c) at least partially transferring the sample of the body fluid onto the test chemical;
d) detecting the detection reaction by using the detector.

Step a) preferably may further imply the step of engaging the puncture element by using the coupling element, preferably at least partially simultaneously to the step of releasing the locking mechanism.

In step b), the coupling element preferably may be driven by the drive element.

In step c), transferring the sample of the body fluid onto the test chemical preferably may be performed by disengaging the coupling element from the puncture element.

As outlined above, the transfer of the body fluid onto the test chemical preferably may take place by one or more transfer elements contained within the sampling element, such as by one or more capillary elements, most preferably by one or more capillary slits contained within the puncture element. As further outlined above, the sampling element may be adapted, during a rearward motion of the puncture element, to bring the transfer element, such as the capillary channel, close to the test chemical, such as close to the test field, in such proximity that the sample contained within the transfer element is transferred onto the test field by wetting. Thus, as an example, the housing may comprise, within the chamber, a guiding which, during a rearward motion of the puncture element, leads the puncture element close to the test chemical. Additionally or alternatively, the puncture element may be pressed onto the test chemical, such as onto the test field.

The analytical device may further be adapted to perform the following step:
e) determining a concentration of at least one analyte in the body fluid by evaluating at least one signal generated by the detector.

For detecting the signal, such as a photometric signal, preferably a signal indicating a remission of a test field, reference may be made to the prior art documents. Thus, a change in color may be detected by using appropriate remission measurements, the change in color indicating a degree of the detection reaction and, thus, indicating the presence of the analyte. These methods are generally known in the art.

In a further aspect of the present invention, a method of generating a sample of the body fluid is disclosed. The method comprises a use of the analytical device according to the present invention, such as according to one or more of the embodiments disclosed above and/or according to one or more of the embodiments disclosed in further detail below. The method comprises the following steps, which, preferably, may be performed in the given order. However, a different order is possible. It is also possible to perform two or more of the method steps simultaneously or in an overlapping fashion. Further, it is possible to perform one, two ore more of the method steps repeatedly. The method may contain additional method steps which are not mentioned in the following. The method steps of the method are as follows:
i) releasing the locking mechanism by using the release element;
ii) driving the puncture element to perform a puncture motion by using the coupling element, thereby generating the sample of the body fluid.

For further details of the method, reference may be made to the disclosure of the analytical device and/or the sampling element, as discussed above. Specifically, the method may be performed such that no medical expert knowledge is required. The method may be performed by a patient or user himself or a medical assistant. The method specifically may be performed such that no substantial physical intervention on the body of the user occurs. Specifically, the puncture motion may be performed such that only a minor opening in the skin of the user is created, such as an opening which produces only minor amounts of body fluids such as blood. Thus, the method specifically may be performed such that amounts of the body fluid of less than 1 ml are created, preferably amounts of less than 0.5 ml or even less than 100 µl, less than 10 µl or even less than 1 µl.

In a further aspect, a use of a position of a compression element for indicating a used or unused state of a sampling element, for the purpose of preventing unwanted reuse of the sampling element is disclosed. As outlined above, the compression element is adapted to increase a pressure of a body fluid within a body tissue of a user in a region of puncturing. Thus, the general aspect of using the position of the compression element for unwanted reuse of the sampling element is proposed.

The sampling element, the analytical device, the method and the use according to the present invention provide a large number of advantages over known devices and methods of this type. Thus, specifically, single tests for one single use may be provided which may be handled independently and which, preferably automatically, may be used for detecting one or more analytes in small body fluid samples. Thus, generally, the chamber, the puncture element, the housing and, optionally, the test chemical may be setup internally as known in the art, such as disclosed in WO 2012/089524 A1 and/or as in WO 2012/140027 A1, wherein the latter specifically discloses single tests. Additionally, the present invention provides a compression element which, generally, may be embodied as an element which is independent from the housing of the sampling element. The compression element is movably mounted to the housing, and, thus, the housing and the compression element form one unit of the sampling element, which may be a disposable sampling element. Simultaneously, the compression element may fulfill the function of indicating an unused state or a used state of the sampling element. Thus, the compression elements may take over the function of the separate locking mechanism as disclosed e.g. in EP 1 459 683 A1 indicating whether the sampling element has been used or not. Consequently, within the present invention of the sampling element, two elements may be combined in an advantageous fashion, i.e. the compression element for pressing body fluid from the region of puncturing and the locking element adapted to prevent a reuse of a used sampling element.

Further, the sampling element may provide a test chemical, preferably a test field. For optical measurements by using an optical detector, in many cases, it is crucial to keep the test field in a fixed position during measurements. Thus, the test field, during measurement, shall not move in order to avoid movement-induced falsifications of the measurement. When using test element magazines with a large area and a large mass, with compression elements mounted to the device rather than to the magazine, this condition typically is rather simple to achieve. Thus, the compression element typically acts on the housing of the analytical device only, separated from the magazine. Contrarily, in single tests or single sampling elements, including one single puncture element and one single test field, the small mass and the small dimensions of the sampling element typically require the compression element to be mounted elsewhere, in order to avoid mechanical influence which might move the test field during measurement, thereby disturbing the optical measurement. Still, the general idea of mounting the compression element to the housing in a movable fashion, as proposed within the present invention, provides the possibility of keeping the housing with the optional test chemical contained therein in a fixed position during sampling and measurement, whereas the movable compression element may move relative to the analytical device and the housing. Thus, the analytical device may comprise a mounting or locking mechanism for keeping the housing in place, whereas the compression element may move from the first position to the second position. A sufficient amount of clearance between the unlocked compression element and the housing may allow for the analytical device to take over the guiding of the compression element from the sampling element. Consequently, the compression and/or the triggering, by using the compression element, may be mechanically independent from the actual measurement.

As for the analytical device, the present invention provides optional means for combining an unlocking of the locking mechanism of the compression element with a driving of the puncture element, in a rather simple fashion. Thus, as outlined above, a release element and a coupling element may be used, wherein, as an example, the release element may be adapted to deform mounting arms of the compression element. The mounting arms preferably provide elastic properties. Thus, as an example, the mounting arms may fully or partially be made of a plastic material, and, thus, may flexibly be deformed by the release element, such as by spreading or forcing apart the mounting arms. Consequently, by using the at least one release element, the locking mechanism may be unlocked without exerting mechanical influence onto the housing and, thus, without exerting mechanical influence onto the optional test field. Thus, by using the release element and the coupling element, as proposed within the present invention, the decoupling and unlocking of the compression element may mechanically be separated from the driving of the puncture element. Further, the compression element may be used as a triggering actuator for triggering the puncture motion, without mechanically moving or shocking the actual chamber within the housing.

Still, the coupling element and the release element, as outlined above and as outlined in further detail below, may be driven by a link mechanism. The link mechanism may as well provide a timing of a releasing action and a coupling action and a puncture action. Thus, generally, a simple actuation mechanism, including an unlocking of the compression element's locking mechanism, may be provided.

Summarizing, within the present invention, the following embodiments are preferred:

Embodiment 1

A sampling element for generating a sample of a body fluid, the sampling element having a housing comprising a chamber with at least one puncture element stored therein, wherein a tip of the puncture element is movable through at least one puncture opening of the housing in order to perforate a skin portion of a user, the sampling element further comprising at least one compression element, wherein the compression element preferably at least partially surrounds the puncture opening, wherein the compression element is adapted to increase a pressure of the body fluid within a body tissue of the user in a region of puncturing when pressed onto the skin portion of the user, wherein the compression element is movably mounted to the housing, wherein the sampling element comprises at least one locking mechanism for releasably locking the compression element in at least two positions, the at least two positions comprising a first position and a second position, the second position being offset from the first position.

Embodiment 2

The sampling element according to the preceding embodiment, wherein the second position is offset from the first position in a longitudinal direction of the sampling element.

Embodiment 3

The sampling element according to the preceding embodiment, wherein the longitudinal direction is a direction of a puncture motion, wherein the puncture motion comprises a forward motion of the tip of the puncture element in order to perforate the skin portion of the user and a backward motion of the tip in order for the puncture element to be restored within the chamber.

Embodiment 4

The sampling element according to the preceding embodiment, wherein the second position is offset from the first position in a direction of the backward motion.

Embodiment 5

The sampling element according to any of the preceding embodiments, wherein the compression element is linearly movable with regard to the housing.

Embodiment 6

The sampling element according to any of the preceding embodiments, wherein the compression element comprises at least one trigger portion adapted to exert a trigger action onto a trigger of an analytical device using the sampling element when the compression element is moved from the first position into the second position.

Embodiment 7

The sampling element according to the preceding embodiment, wherein the trigger portion comprises an edge of the compression element, preferably an edge of a mounting portion of the compression element and more preferably an edge of at least one mounting arm of the compression element.

Embodiment 8

The sampling element according to any of the preceding embodiments, wherein the compression element is movably mounted to the housing such that, when the locking mechanism is released and when the compression element is pressed onto the skin portion of the user, the compression element is moved from the first position into the second position.

Embodiment 9

The sampling element according to any of the preceding embodiments, wherein the compression element comprises at least one annular protrusion being adapted to be pressed onto the skin portion in the region of puncturing, the compression element further having a mounting portion movably mounted to the housing.

Embodiment 10

The sampling element according to the preceding embodiment, wherein the mounting portion comprises at least one mounting arm which is slidably guided in a guiding of the housing.

Embodiment 11

The sampling element according to the preceding embodiment, wherein the guiding comprises at least one guide rail.

Embodiment 12

The sampling element according to any of the two preceding embodiments, wherein the mounting arm is a snap arm adapted to snap into at least one corresponding notch in the first position and the second position.

Embodiment 13

The sampling element according to any of the preceding embodiments, wherein the housing comprises at least one guiding, preferably at least one guide rail, wherein the compression element slidably is mounted to the guiding.

Embodiment 14

The sampling element according to the preceding embodiment, wherein the guiding extends along a longitudinal axis of the sampling element.

Embodiment 15

The sampling element according to any of the preceding embodiments, wherein the locking mechanism comprises a releasable snap fit connection.

Embodiment 16

The sampling element according to any of the preceding embodiments, wherein the compression element comprises at least one snap arm which is adapted to releasably snap into a first notch when the compression element is in the first position and to snap into a second notch when the compression element is in the second position.

Embodiment 17

The sampling element according to any of the preceding embodiments, wherein at least one of the at least two positions functions as an indication whether the sampling element has been used or not.

Embodiment 18

The sampling element according to any of the preceding embodiments, wherein the sampling element is a disposable sampling element adapted for single use, wherein the first position is an unused position and wherein the second position is a used position.

Embodiment 19

The sampling element according to any of the preceding embodiments, wherein at least a part of the compression element protrudes from the housing and forms a protrusion from the sampling element when the compression element is in the second position.

Embodiment 20

The sampling element according to any of the preceding embodiments, wherein the puncture element comprises at least one capillary adapted to receive body fluid from the region of puncturing.

Embodiment 21

The sampling element according to the preceding embodiment, wherein the puncture element is a micro-sampler having at least one capillary slot.

Embodiment 22

The sampling element according to any of the preceding embodiments, wherein the sampling element further comprises at least one test chemical adapted for performing at least one detectable detection reaction in the presence of at least one analyte to be detected, wherein the sampling element is adapted to transfer body fluid onto the test chemical.

Embodiment 23

The sampling element according to the preceding embodiment, wherein the test chemical is comprised in at least one test field.

Embodiment 24

The sampling element according to any of the two preceding embodiments, wherein the test chemical is accessible from the chamber.

Embodiment 25

The sampling element according to the preceding embodiment, wherein the sampling element is adapted to take up the sample of the body fluid with the puncture element in a puncture motion of the puncture element and to transfer the sample of the body fluid from the puncture element onto the test chemical.

Embodiment 26

The sampling element according to the preceding embodiment, wherein the sampling element is adapted to bring the puncture element close to the test chemical when the puncture element is pulled back into the chamber.

Embodiment 27

The sampling element according to any of the preceding embodiments, wherein the housing further comprises at least one actuator opening adapted for a coupling element to enter the chamber and to engage with the puncture element in order to drive the puncture element for a puncture motion.

Embodiment 28

The sampling element according to any of the preceding embodiments, wherein the puncture element comprises at least one connection element adapted to engage with at least one coupling element for being driven to perform a puncture motion.

Embodiment 29

The sampling element according to the preceding embodiment, wherein the connection element comprises at least one opening adapted to be engaged by a hook of the coupling element.

Embodiment 30

The sampling element according to any of the preceding embodiments, wherein the sampling element contains precisely one puncture element.

Embodiment 31

An analytical device, the analytical device being adapted for using the sampling element according to any of the preceding embodiments, the analytical device comprising at least one coupling element adapted for driving the puncture element to perform a puncture motion, the analytical device further comprising at least one release element, the release element being adapted for releasing the locking mechanism of the sampling element in the first position before performing the puncture motion in order to allow for the compression element of the sampling element to be moved from the first position into the second position.

Embodiment 32

The analytical device according to the preceding embodiment, wherein the coupling element comprises at least one hook adapted to engage with an opening of the puncture element of the sampling element.

Embodiment 33

The analytical device according to any of the two preceding embodiments, wherein the release element comprises at least one release element bar adapted to be pushed in between at least a part of the compression element and the housing of the sampling element in order to release the locking mechanism.

Embodiment 34

The analytical device according to the preceding embodiment, wherein the at least one release element bar comprises a wedge.

Embodiment 35

The analytical device according to any of the preceding embodiments referring to an analytical device, wherein the coupling element and the release element are driven via a link mechanism, preferably by two drives acting on a link mechanism which transmits the movements of the two drives onto the coupling element and the release element in a joint manner.

Embodiment 36

The analytical device according to the preceding embodiment, wherein the link mechanism comprises at least one lever connected both to the coupling element and the release element.

Embodiment 37

The analytical device according to any of the preceding embodiments referring to an analytical device, wherein the coupling element and the release element are mounted on a common guide, such as a common linear guide, and, preferably, are independently movable on the guide.

Embodiment 38

The analytical device according to any of the preceding embodiments referring to an analytical device, wherein the release element is spring-biased in order to reengage the locking mechanism after triggering the sampling action.

Embodiment 39

The analytical device according to any of the preceding embodiments referring to an analytical device, wherein the analytical device further comprises at least one trigger adapted to initiate the coupling element to drive the puncture motion, wherein the trigger is adapted to be actuated by the compression element when the compression element is moved from the first position into the second position.

Embodiment 40

The analytical device according to any of the preceding embodiments referring to an analytical device, wherein the analytical device is further adapted to prevent the coupling element to drive the puncture motion when the compression element is found to be in the second position, thereby preventing a reuse of a used sampling element.

Embodiment 41

The analytical device according to any of the preceding embodiments referring to an analytical device, wherein the analytical device is further adapted to prevent the sampling element to be located in an application position of the analytical device when the compression element is found to be in the second position, thereby preventing a reuse of a used sampling element.

Embodiment 42

The analytical device according to any of the preceding embodiments referring to an analytical device, wherein the analytical device further comprises at least one sampling element according to any of the preceding embodiments referring to a sampling element.

Embodiment 43

The analytical device according to the preceding embodiments, wherein the analytical device comprises a plurality of the sampling elements.

Embodiment 44

The analytical device according to any of the preceding embodiments referring to an analytical device, wherein the analytical device comprises an application position, wherein the analytical device is adapted to subsequently move sampling elements into the application position and to perform a puncture motion by using the sampling element in the application position.

Embodiment 45

The analytical device according to any of the preceding embodiments referring to an analytical device, wherein the analytical device further comprises at least one detector adapted to detect at least one detection reaction of a test chemical of the sampling element.

Embodiment 46

The analytical device according to the preceding embodiment, wherein the detector is an optical detector adapted to detect an optically detectable detection reaction of the test chemical.

Embodiment 47

The analytical device according to the preceding embodiment, wherein the optical detector comprises at least one light source adapted to illuminate the test chemical of the sampling element.

Embodiment 48

The analytical device according to the preceding embodiment, wherein the optical detector comprises at least one light source adapted to illuminate the test chemical of the sampling element.

Embodiment 49

The analytical device according to any of the two preceding embodiments, wherein the optical detector comprises at least one light-sensitive element adapted to detect light propagating from the test chemical to the detector.

Embodiment 50

The analytical device according to any of the four preceding embodiments, wherein the analytical device is adapted to perform the following steps:
a) releasing the locking mechanism by using the release element;
b) driving the puncture element to perform a puncture motion by using the coupling element, thereby generating the sample of the body fluid;
c) at least partially transferring the sample of the body fluid onto the test chemical; and
d) detecting the detection reaction by using the detector.

Embodiment 51

The analytical device according to the preceding embodiment, wherein the analytical device is further adapted to perform the following step:
e) determining a concentration of at least one analyte in the body fluid by evaluating at least one signal generated by the detector.

Embodiment 52

A method of generating a sample of a body fluid, the method comprising a use of the analytical device according to any of the preceding embodiments referring to an analytical device, the method comprising the following steps:
i) releasing the locking mechanism by using the release element;
ii) driving the puncture element to perform a puncture motion by using the coupling element, thereby generating the sample of the body fluid.

Embodiment 53

A use of a position of a compression element adapted to increase a pressure of a body fluid within a body tissue of a user in a region of puncturing, the compression element being movably mounted to a housing of a sampling element, for indicating a used or unused state of the sampling element for preventing reuse of the sampling element.

SHORT DESCRIPTION OF THE FIGURES

Further optional features and embodiments of the invention will be disclosed in more detail in the subsequent description of preferred embodiments, preferably in conjunction with the dependent claims. Therein, the respective optional features may be realized in an isolated fashion as well as in any arbitrary feasible combination, as the skilled person will realize. The scope of the invention is not restricted by the preferred embodiments. The embodiments are schematically depicted in the Figures. Therein, identical reference numbers in these Figures refer to identical or functionally comparable elements.

Figure 2:
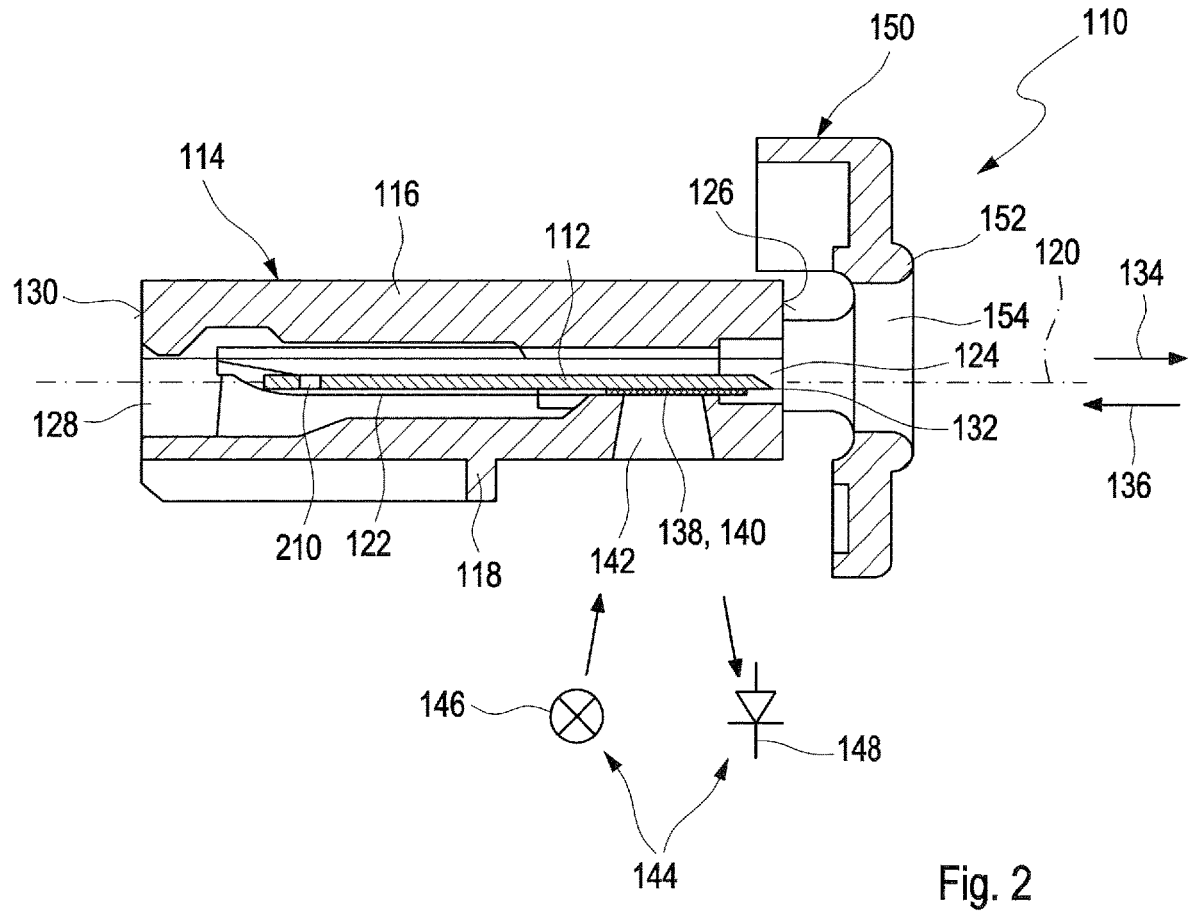
Figure 3:
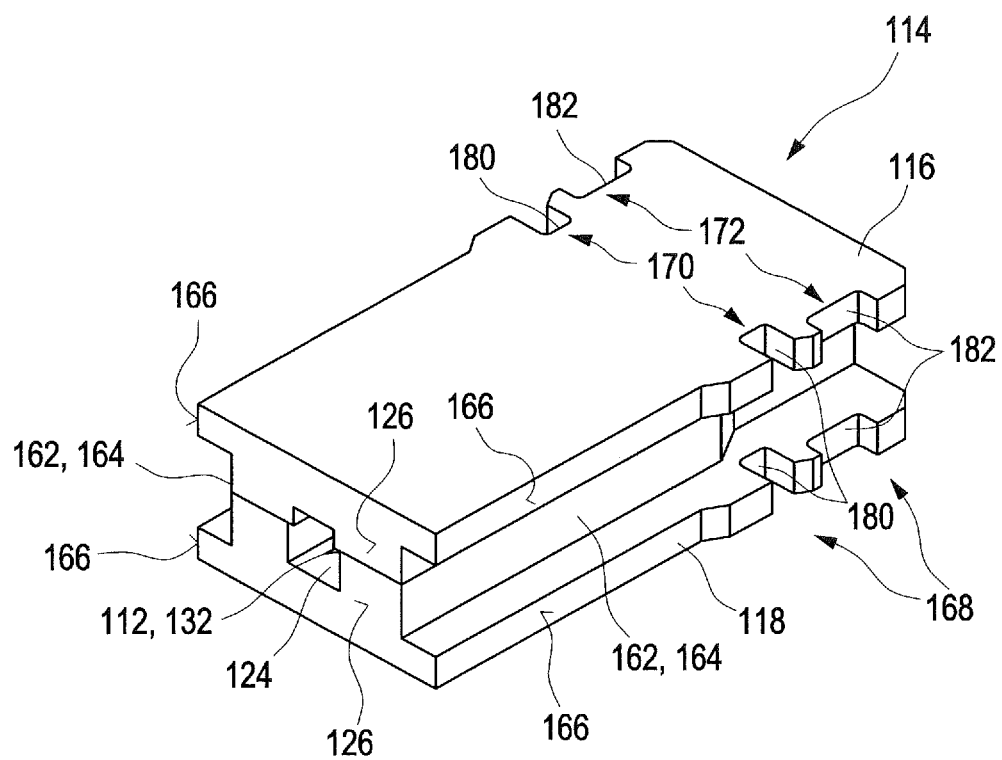
Figure 5:
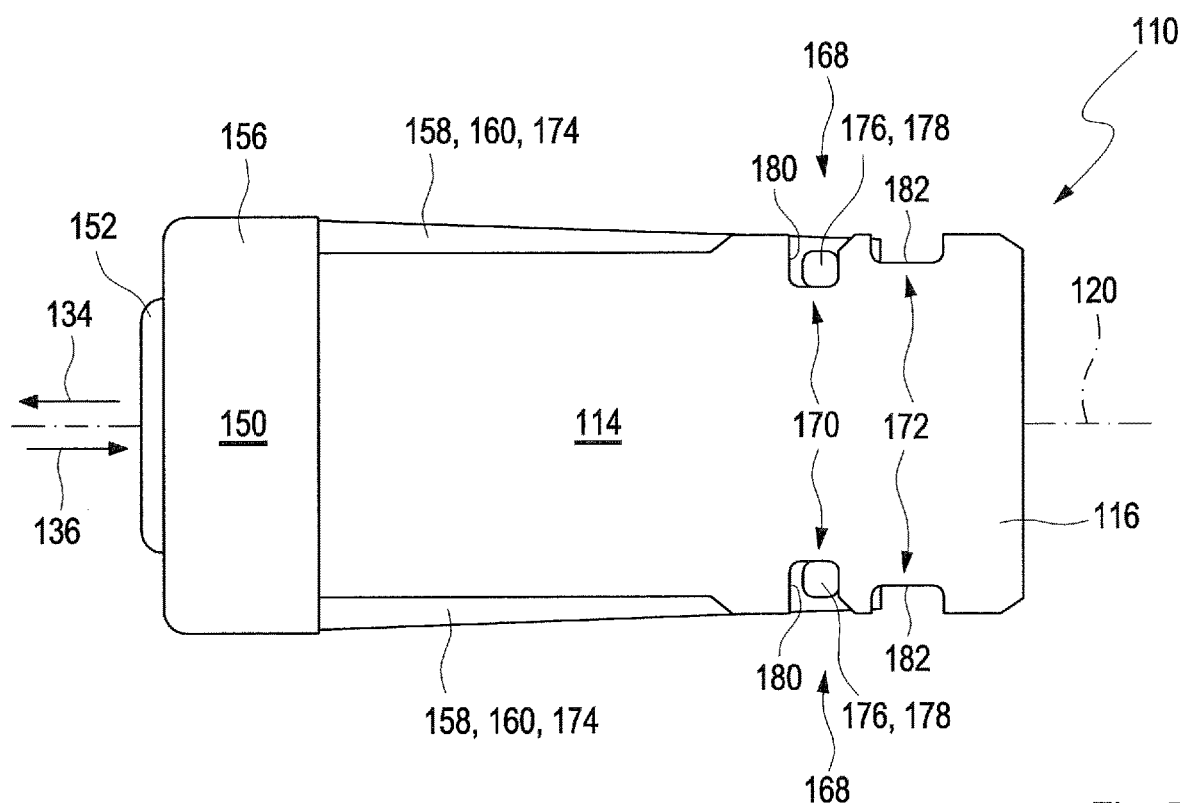
Figure 6:
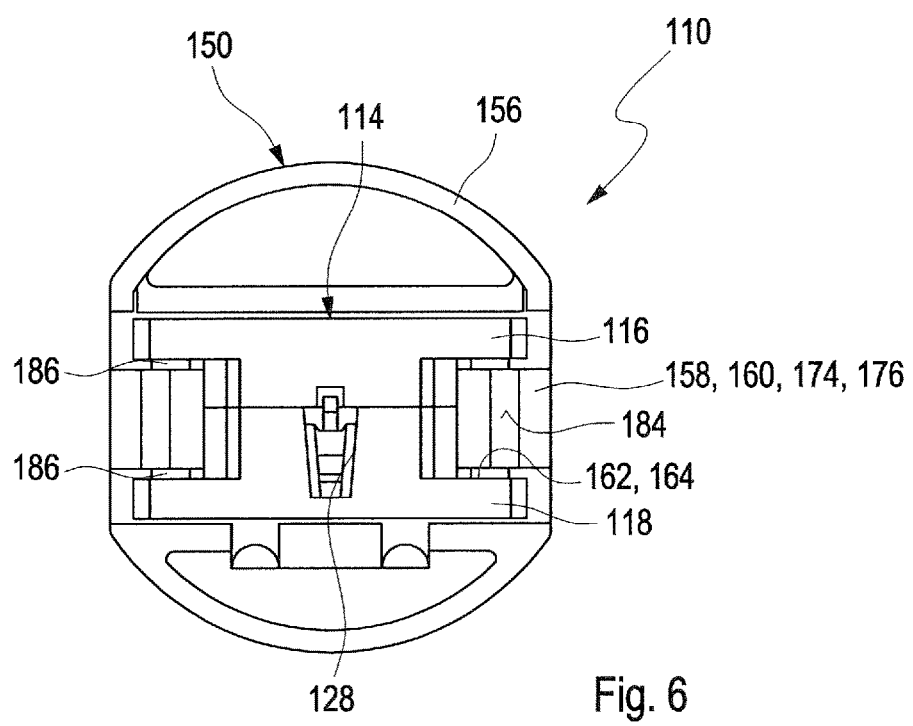
Figure 7:
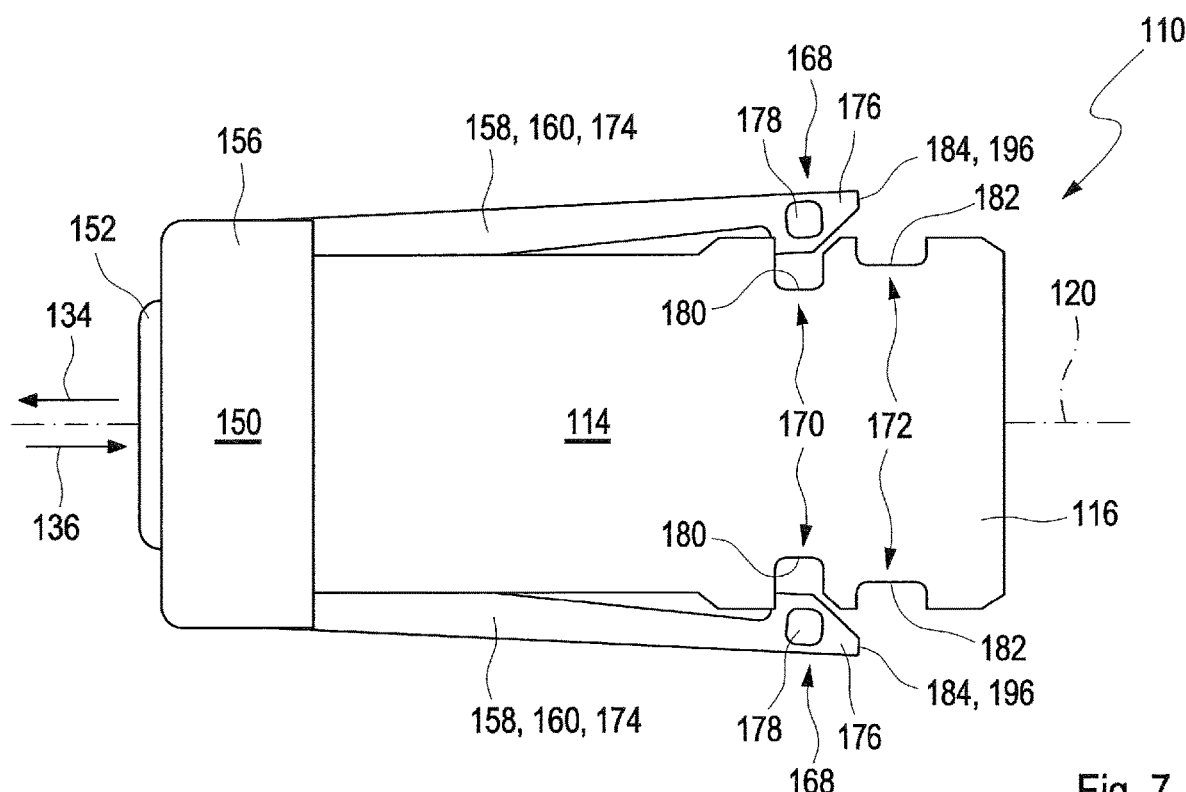
Figure 8:
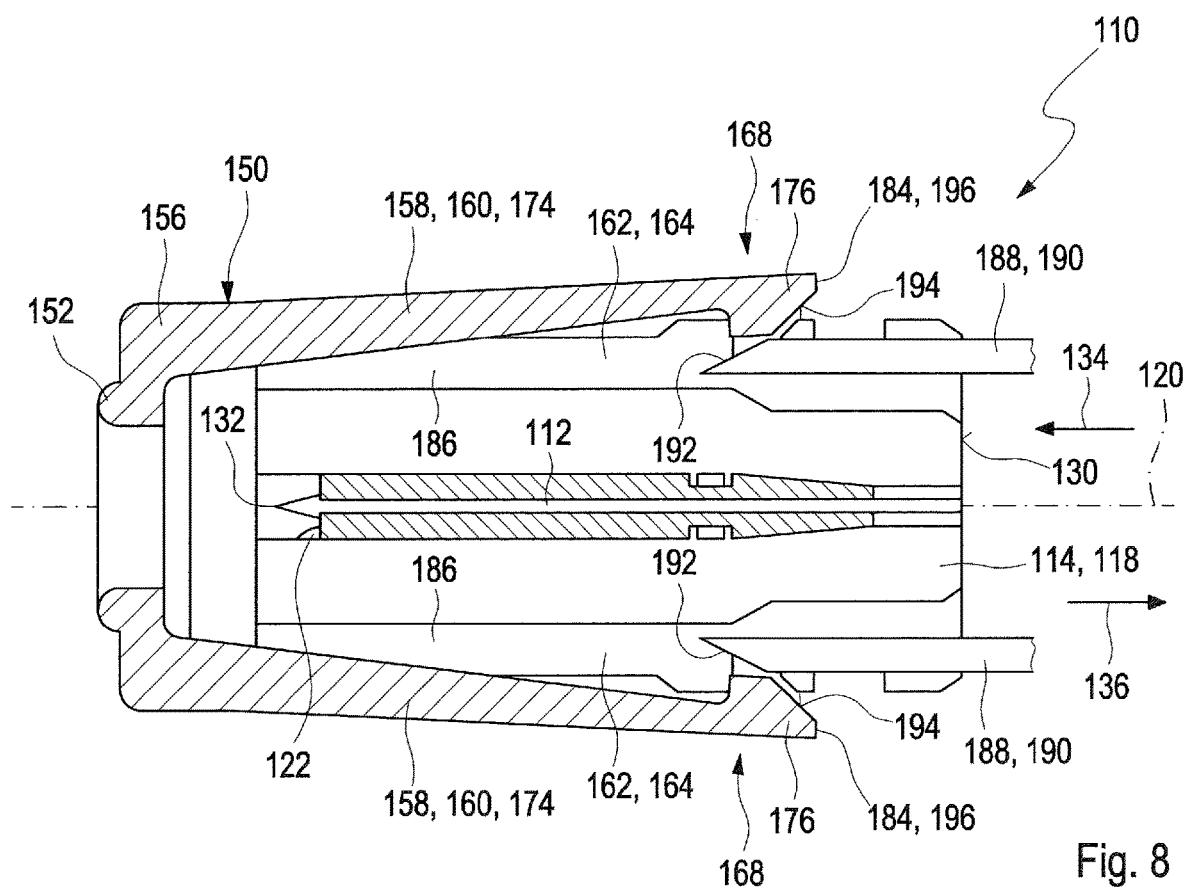
Figure 9:
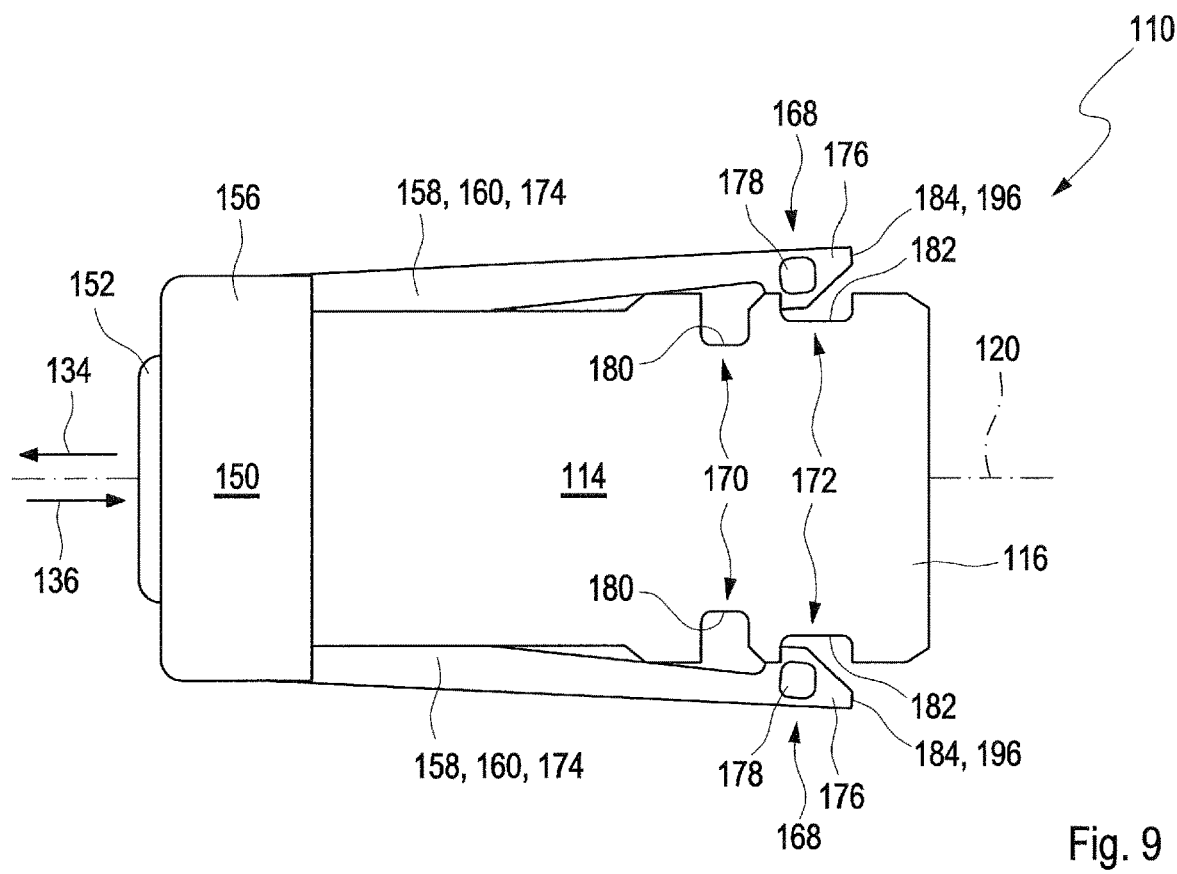
Figure 10:
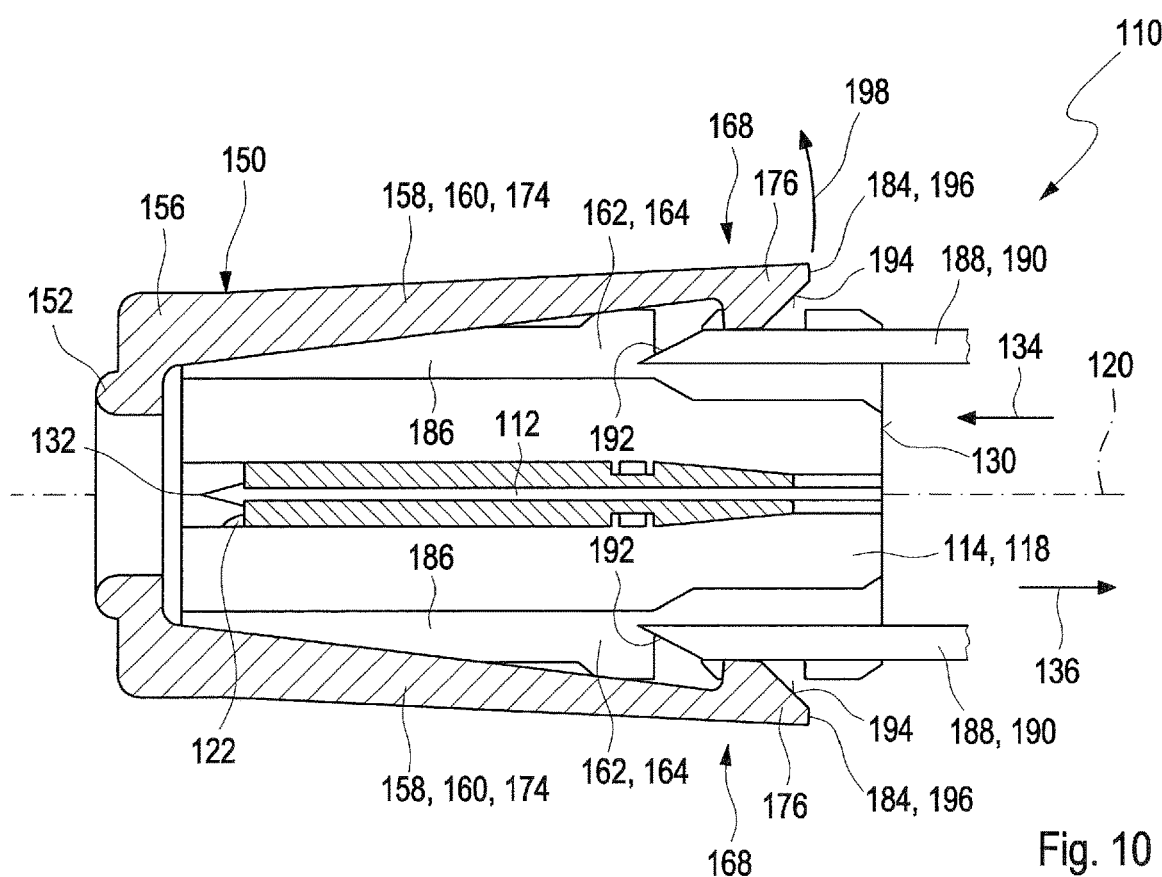
Figure 11:
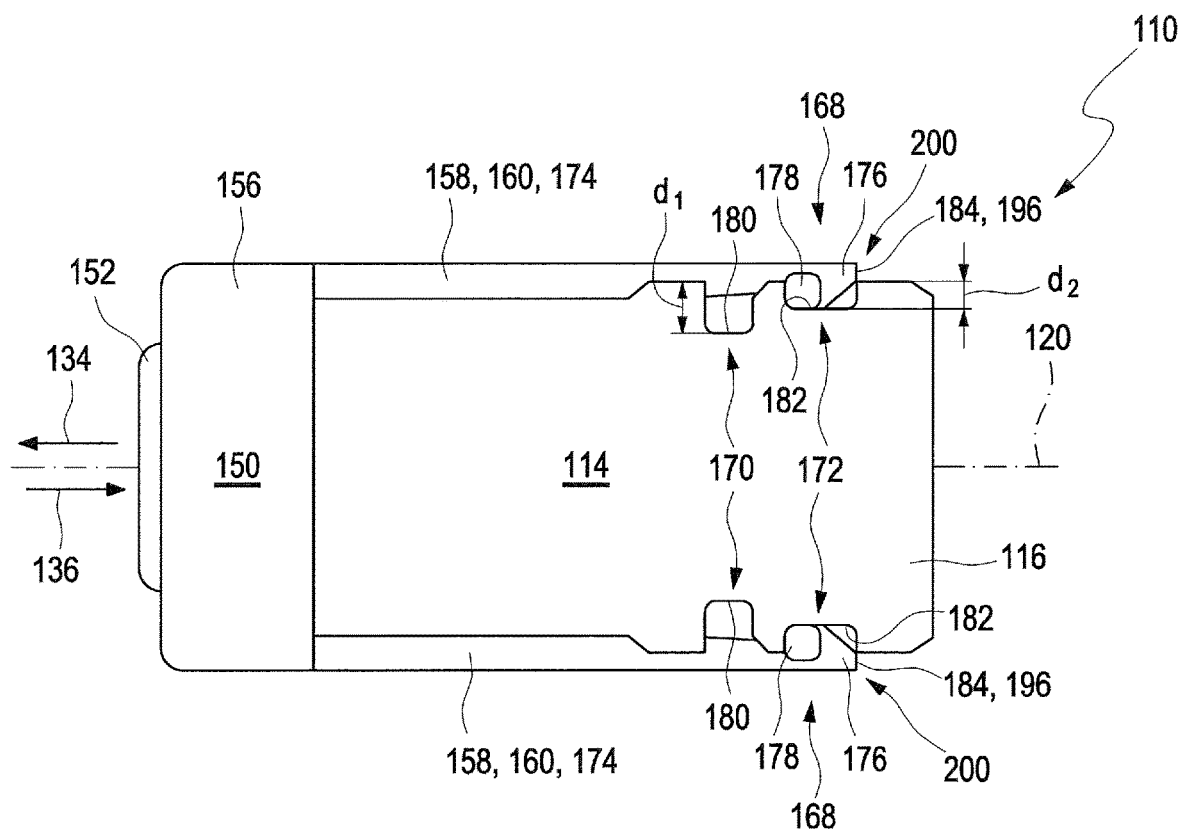
Figure 12:
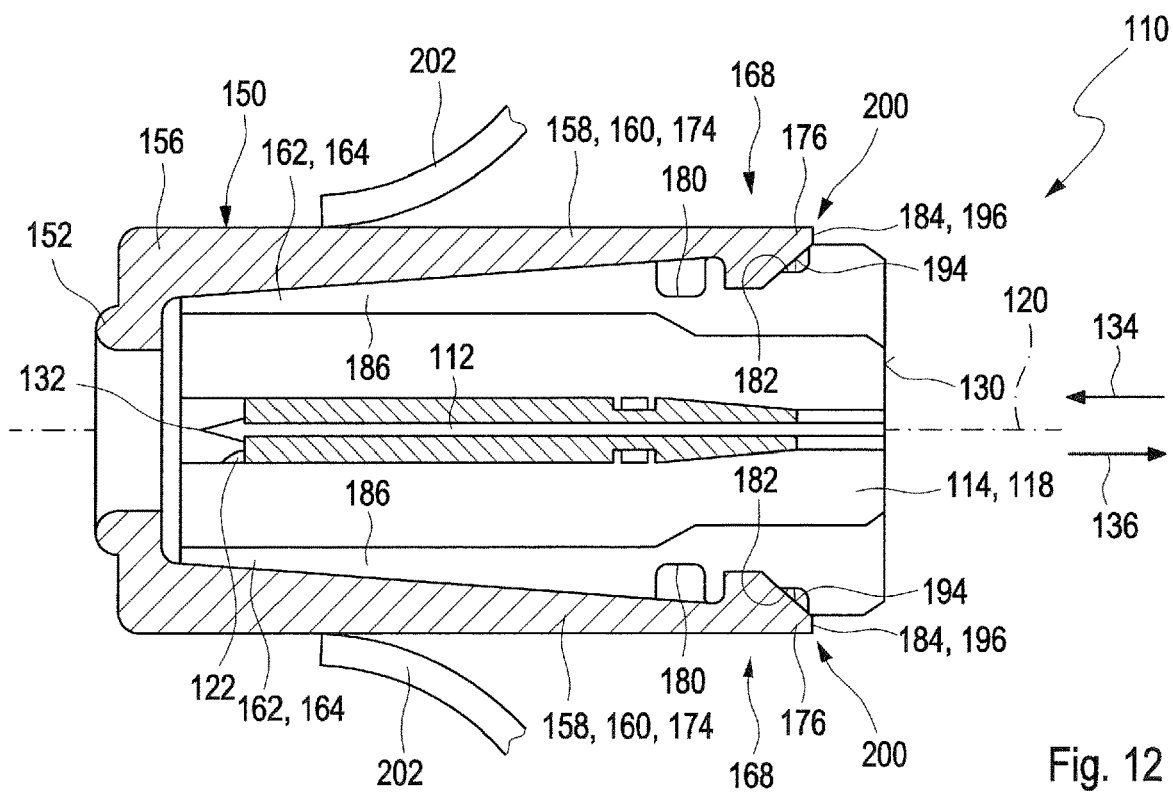
Figure 13:
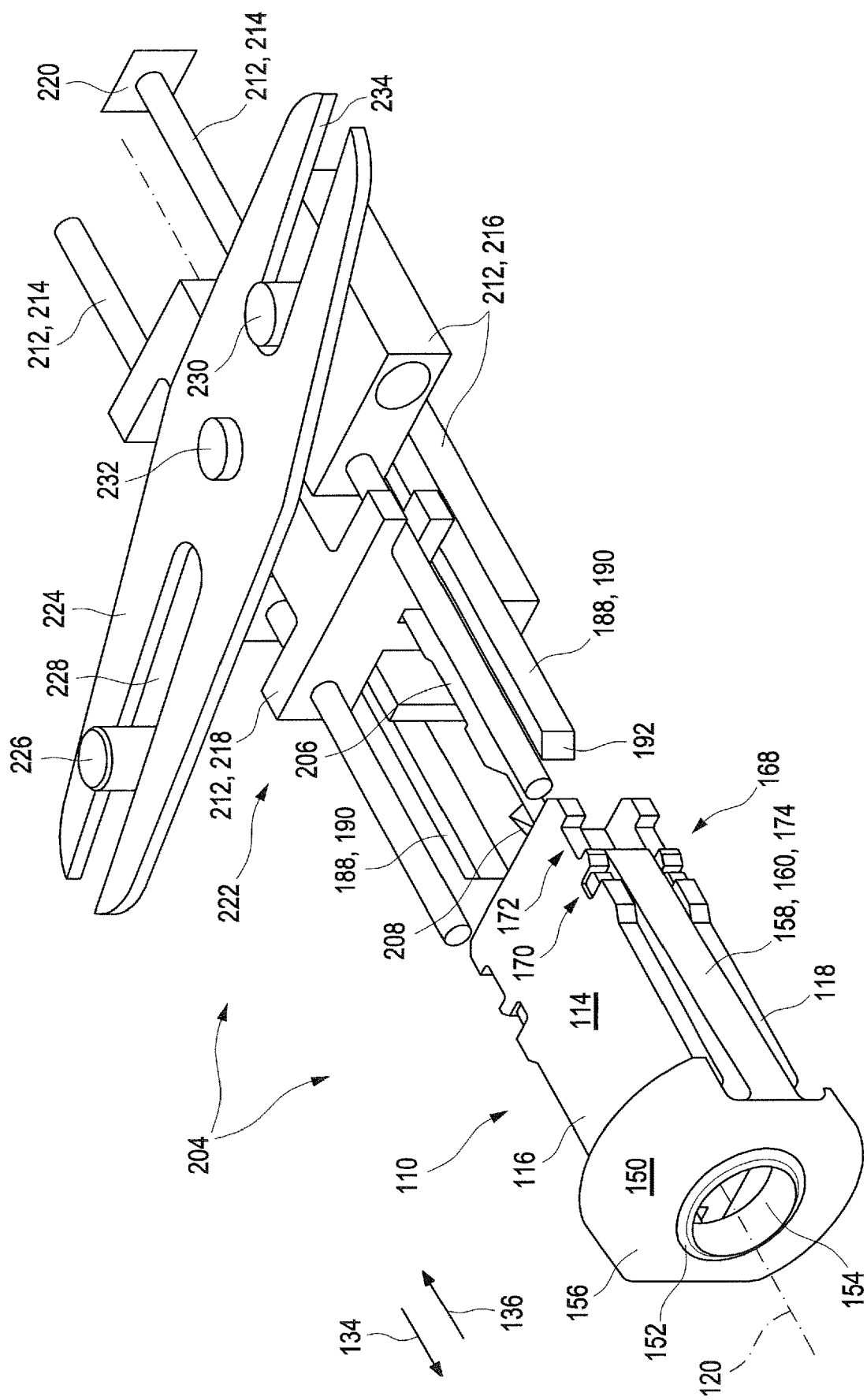
Figure 14:
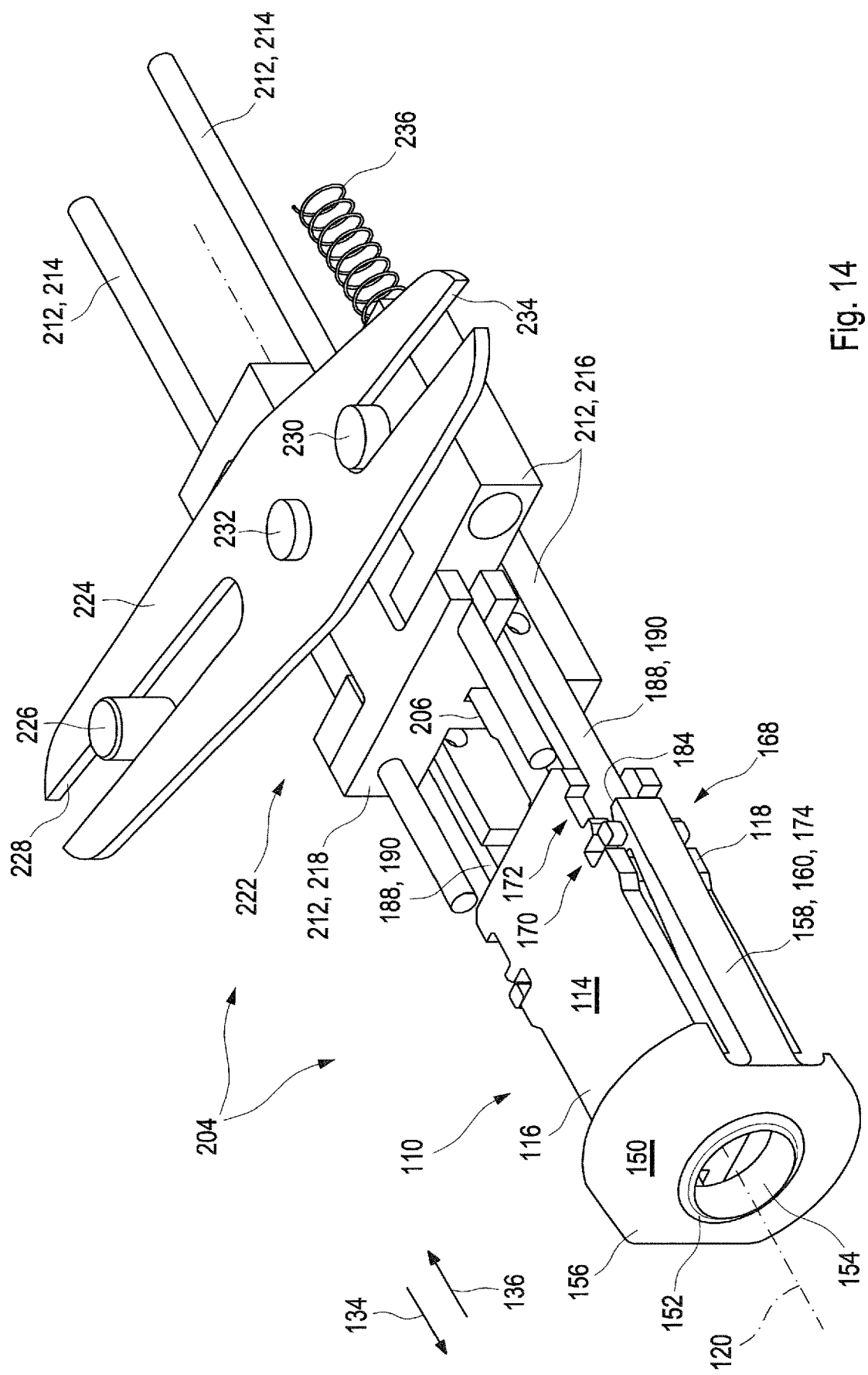
Figure 15:
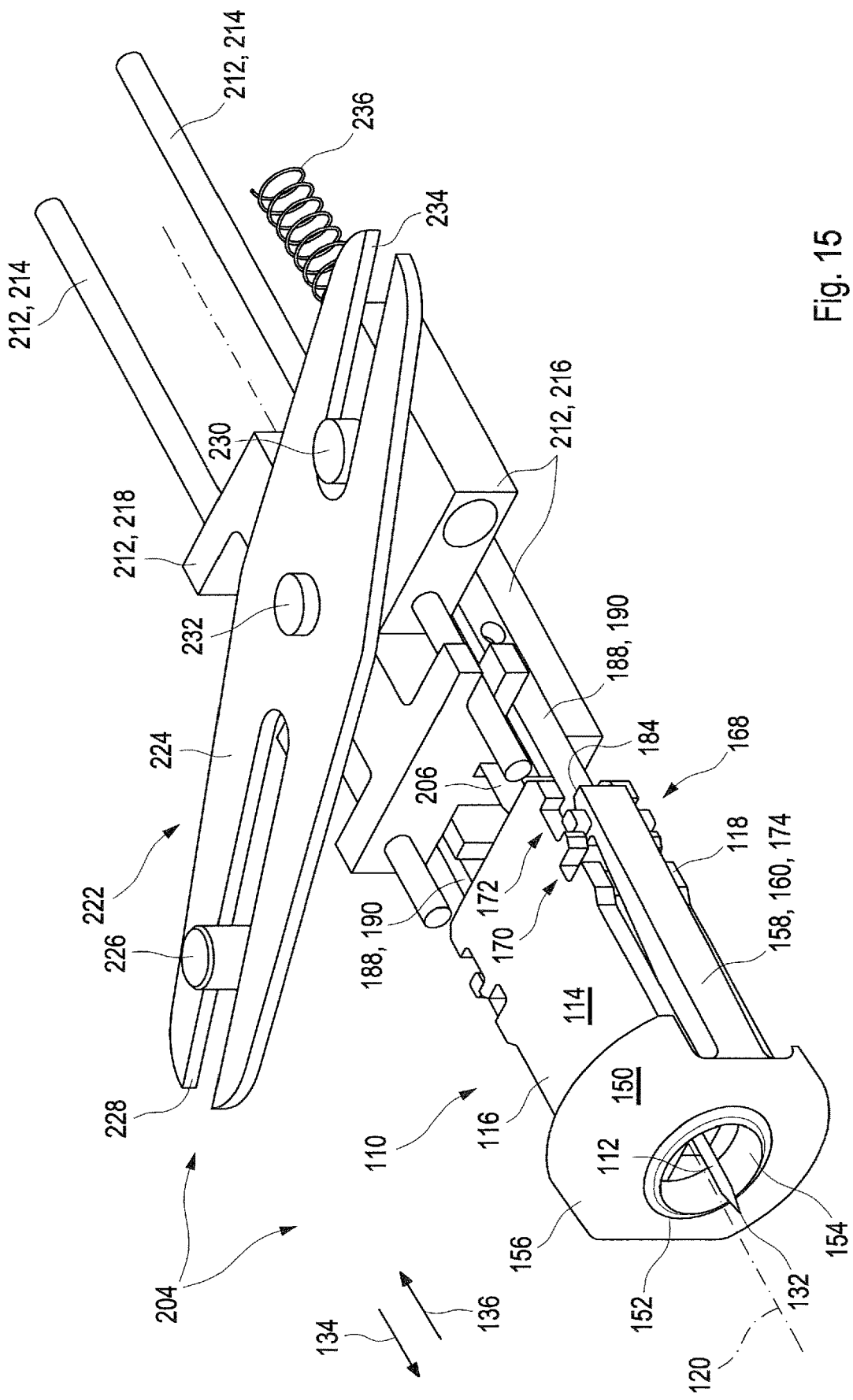
Figure 16:
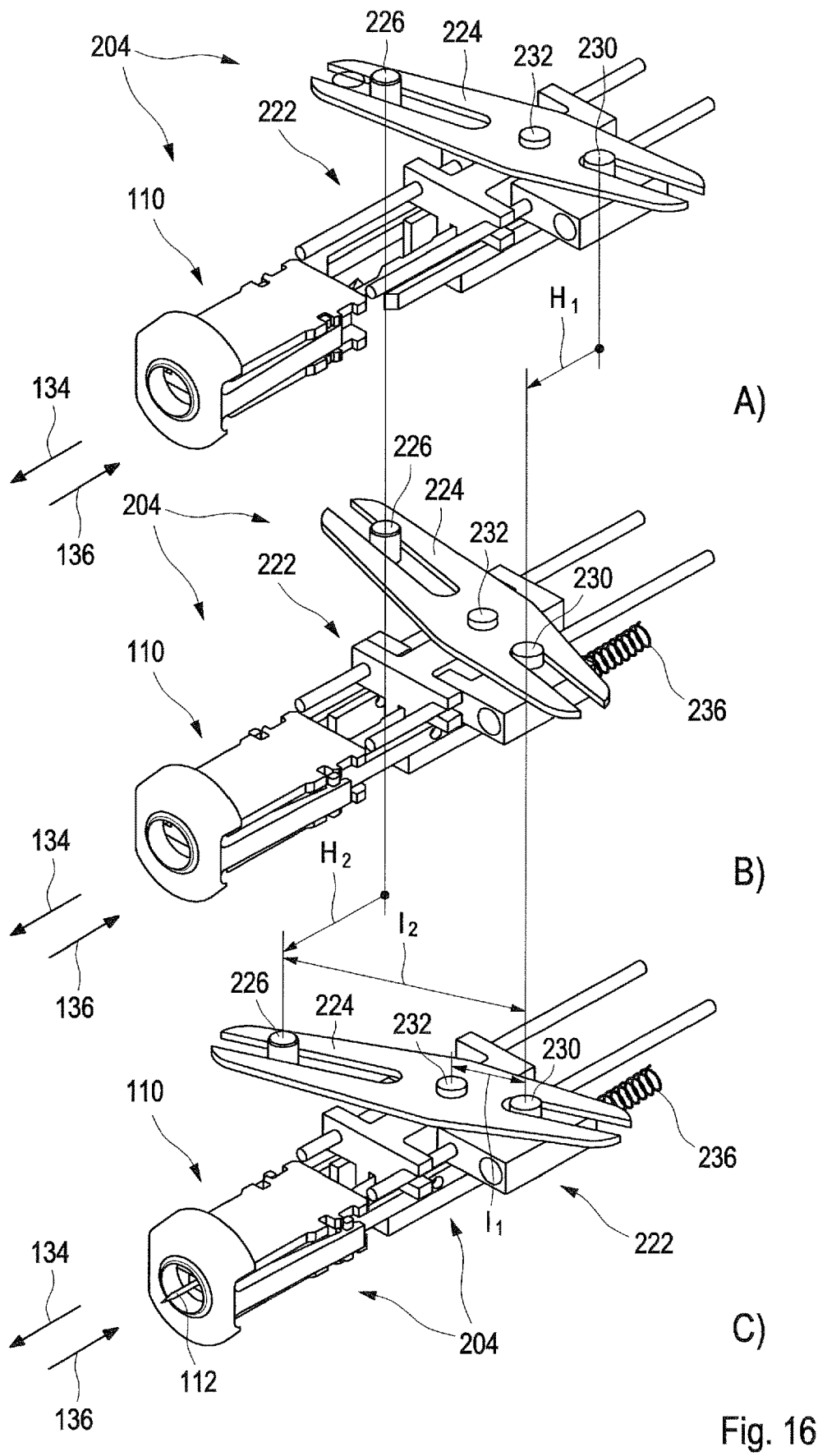

In the figures:
FIG. 1 shows a perspective view of a sampling element;
FIG. 2 shows a cross-sectional view along a longitudinal axis of the sampling element of FIG. 1;
FIG. 3 shows a perspective view of a housing of the sampling element of FIG. 1;
FIG. 4 shows a perspective view of a compression element of the sampling element of FIG. 1;
FIG. 5 shows a top view of a sampling element with the compression element in a first position;
FIG. 6 shows a cross-sectional view of the sampling element of FIG. 1 in a plane perpendicular to a longitudinal axis;
FIG. 7 shows a top view of the sampling element with a locking mechanism unlocked, the compression element still in the first position;
FIG. 8 shows a cross-sectional view of the setup of FIG. 7, with a release actuator forcing apart the mounting arms of the compression element;
FIG. 9 shows a top view of the sampling element, with the compression element in the second position and the locking mechanism still unlocked;
FIG. 10 shows a cross-sectional view of FIG. 9, with the release actuator still in place;
FIG. 11 shows a top view of the sampling element, with the compression element in the second position and the locking mechanism locked;
FIG. 12 shows a cross-sectional view of the setup of FIG. 11, with the release actuator removed;
FIG. 13 shows a setup of an analytical device with the sampling element of FIG. 1, in an initial position;
FIG. 14 shows the analytical device of FIG. 13 in a preparation movement for releasing the locking mechanism of the sampling element;
FIG. 15 shows the analytical device performing a puncture motion; and FIGS. 16A-16C show a sequence of motions of a link mechanism of the analytical device performing a preparation motion and a puncture motion.

DETAILED DESCRIPTION OF THE EMBODIMENTS

In FIGS. 1-12, various views of an embodiment of a sampling element 110 for generating and, in this case, optionally analyzing a sample of a body fluid are depicted. The analysis, in this case, as an example, may be adapted for determining the concentration of one or more analytes contained within the sample of the body fluid, such as glucose within blood and/or interstitial fluid. In the following, when explaining the setup and the functions of the sampling element, reference will be made to FIGS. 1-12 in conjunction.

In FIG. 1, a perspective view of the sampling element 110 is given. The sampling element 110 is a single sampling element, adapted for a single use, i.e. a single test containing precisely one puncture element 112, as will be explained with regard to FIG. 2 below. The sampling element comprises a housing 114, which, as an example, may be made of a plastic material, such as by injection molding. As an example, the housing 114 may be composed of one or more parts, such as an upper housing part 116 and a lower housing part 118. The housing, as can be seen in a cross-sectional view along a longitudinal axis 120 in FIG. 2, which may be an axis of the puncture motion and/or an axis of a longitudinal extension of the puncture element 112, contains a chamber 122, preferably a single chamber 122.

Within the chamber 122, the puncture element 112 is stored. The chamber 122 comprises a puncture opening 124 at a front face 126 of the housing 114 and an actuator opening 128 at a rear face 130. Through the actuator opening 128, a coupling element, which will be explained in further detail below, may enter the chamber 122, engage with the puncture element 112, and drive a tip 132 of the puncture element to exit the puncture opening 124 in a forward direction 134, in order to perforate a skin portion of a user in a region of puncturing. Afterwards, preferably, the coupling element may retract the tip 132 into the chamber 122 in a rearward direction 136, in order to safely restore the puncture element 112 within the chamber 122.

Further, during the rearward movement, body fluid taken up by the puncture element 112, which preferably may comprise one or more capillary elements, such as one or more open capillary slits, may be transferred onto a test field 138 having at least one test chemical contained therein. The test field 138 is accessible from the interior of the chamber 122 in order to allow for a transfer of the sample fluid from the puncture element 112 onto the test field 138. As an example, the test field 138 may cover an interior portion of a detector opening 142 which may form a window within the housing 114, thereby allowing for a detector 144 (symbolically depicted in FIG. 2), which may be part of an analytical device, to illuminate the test field by a light source 146 and to detect light propagating from the test field 138 to the detector 144 by using at least one light-sensitive element 148. For further potential details of the setup of the chamber 122 and the test field 138, as an example, reference may be made to the setup disclosed in WO 2012/140027 A1 and/or the setup disclosed in WO 2012/089524 A1. Still, other embodiments are feasible.

The sampling element 110 further comprises a compression element 150 which is adapted to increase a pressure of the body fluid within a body tissue of the user in a region of puncturing when pressed onto the skin portion of the user. Thus, as an example, a point in which the longitudinal axis 120 hits the skin portion of the user when the sampling element is pressed onto the skin portion may determine a region of puncturing, i.e. a region in which the tip 132 perforates the skin portion, thereby creating a puncture opening. The compression element 150 may comprise an annular protrusion 152 which, preferably, forms a rim of a compression opening 154 within the compression element 150.

The compression element 150 preferably at least partially surrounds the puncture opening 124. As used herein, the compression element 150 at least partially surrounding the puncture opening 124 is to be understood that, when projected onto a common plane perpendicular to the longitudinal axis 120, the puncture opening 124 at least partially is visible through the compression element 150, such as through the compression opening 154. Then pressed onto the skin portion of the user, the compression element 150, specifically the annular protrusion 152, forms a convulsion of the skin portion which extends into the compression opening 154 and in which a pressure of the body fluid is increased as compared to body tissue outside the annular protrusion 152. This convulsion may be reached by the tip 132, since the compression element 150 fully or partially surrounds the puncture opening 124 and, thus, the convulsion is located in front of the puncture opening 124. Thus, by creating an increased pressure within this region, body fluid is expressed from a puncture opening created by the tip 132 within the skin portion.

As will be explained in further detail with regard to FIGS. 3 and 4 below, the housing 114 and the compression element 150 are separate elements which may be manufactured independently. Thus, as outlined above, the housing 114 may be made of separate pieces, such as an upper housing part 116 and a lower housing part 118. The compression element 150 may comprise the annular protrusion 152, preferably at an edge of the compression of the compression opening 154. The annular protrusion may act as a compression ring and may be located in a body 156 of the compression element 150. The body 156 may fully or partially cover the front face 126 of the housing 114.

The compression element 150, preferably the body 156, is movably mounted to the housing 114, preferably linearly movable with regard to the housing 114, most preferably in the direction of the longitudinal axis 120. For this purpose, the compression element 150 may comprise a mounting portion 158 which, in this embodiment, may comprise two or more mounting arms 160. The mounting arms 160 preferably, in this embodiment or in other embodiments, are flexible mounting arms 160. The mounting arms 160 may be guided in an appropriate guiding 162 of the housing 114, which, as an example, may comprise guide rails 164 which are adapted to receive the mounting arms 160. The guide rails 164 preferably comprise longitudinal grooves extending along side faces 166 of the housing 114, preferably at least essentially parallel to the longitudinal axis 120, i.e. preferably parallel with a tolerance of no more than 20°, more preferably of no more than 10° and most preferably of no more than 5°.

The sampling element 110 further comprises a locking mechanism 168 which allows for releasably locking the compression element 150 in at least two positions, the at least two positions comprising a first position 170 and a second position 172. The locking mechanism 168 comprises, in this embodiment, components of the mounting portion 158 of the compression element 150 and components of the housing 114. Thus, in this embodiment, the mounting arms 160 are designed as flexible snap arms 174 having snap hooks 176 and/or protrusions 178 which may snap into corresponding elements of the housing 114. Thus, the housing may comprise first notches 180 in the first position 170 and second notches 182 in the second position 172, into which the snap arms 174 may lock. Thus, the snap arms 174 may be locked in the two positions 170, 172. The snap arms 174, the snap hooks 176, the protrusions 178 and the first and second notches 180, 182 thus all form part of the locking mechanism 168. In order to release the locking mechanism 168 and bring the locking mechanism into an unlocked state, the snap arms 174 may be forced apart, and, thus, the protrusions 178 may be forced out of the corresponding notches 180, 182. When released, the compression element 150 may freely move from the first position 170 into the second position 172, such as when a force is exerted onto the annular protrusion 152, by pressing the body 156 of the compression element 150 onto the skin portion of the user.

In FIG. 5, a top view of the sampling element 110 is shown, with the locking mechanism 168 locked and the compression element 150 being in the first position 170. In this position, as can be seen, the snap arms 174 and the protrusions 178 are locked in the first notches 180, on both sides of the housing 114.

As will be outlined in further detail below, a rear part of the mounting portion 158, in this embodiment a rear part of the mounting arms 160, forms a trigger portion 184 and, in a used state, protrudes from the sampling element 110. As can be seen in FIG. 5, this is not the case when the compression element 150 is in the first position. Thus, in the first position, preferably, the snap arms 174 do not protrude from the housing 114. Similarly, in FIG. 6, a cross-sectional view perpendicular to the longitudinal axis of extension is shown, in a direction of view of the forward direction 134. As can be seen in these figures, the snap arms 174 do not protrude from the housing 114 in a lateral direction when the snap arms 174 are locked in this first position.

Still, as can also be seen in FIG. 6, preferably, the guiding 162 is designed such that the mounting arms 160 are guided with a clearance 186. Thus, when the locking mechanism 168 is released, preferably, the compression element 150 may move freely from the housing 114, with clearance in all spatial dimensions. Thus, due to this clearance, a movement of the compression element 150 relative to the housing 114 does not imply any mechanical influence exerted onto the housing 114 and, thus, does not disturb an optical measurement. Most preferably, during that movement, the compression element 150 and the housing 114 do not touch or, at least, have a minimum contact, such as in the region of the snap hooks 176, only.

For preparing a measurement, as will be outlined in further detail below, the sampling element 110 is docked to an analytical device and then the mounting arms 160, which preferably are elastic or flexible mounting arms 160, are forced apart such that the compression element 150 does not provide any significant contact to the housing 114 any longer. This is shown in FIGS. 7 and 8. Thus, FIG. 7 shows the sampling element, as in FIG. 5, with the mounting arms 160 forced apart. By forcing apart these mounting arms 160, the snap hooks 176 and the protrusions 178 are unlocked from the first notch 180, and the locking mechanism is unlocked. In FIG. 7, a cross-sectional view in a plane parallel to the longitudinal axis 120 is shown which indicates that this forcing apart of the mounting arms 160 may take place by one or more appropriate release elements 188 having release element bars 190 with wedges 192 at their front ends, which glide along gliding surfaces 194 of the snap hooks 176, when pushed in the forward direction 134.

The release element bars 190, preferably, are fully or partially made of a less flexible material, such as a metal. Thus, by spreading apart the mounting arms 160, the clearance 186 is increased, the locking mechanism 168 is unlocked, and, thus, the compression element 150 is freely movable in a direction parallel to the longitudinal axis 120, without mechanically affecting the housing 114 with the chamber 122 disposed therein. This avoidance of mechanical influences may be essential for measurement, since, typically, in optical measurements, at least two measurement values have to be taken at two different points in time, one before the test field 138 is wetted by the body fluid (dry value) and at least one after wetting. Most preferably, the test field 138, in between these at least two measurements, shall not move relative to the detector 144, in order to avoid falsifications of the measurement.

Thus, as can be seen in FIG. 8, the locking mechanism 168 allows for a mechanical simple unlocking by the release element 188. In the unlocked state, the protrusions 178 of the snap hooks 176 are lifted from the first notch 180 and, thus, the compression element 150 may move in a rearward direction 136, from the first position 170 to the second position 172. This movement of the compression element 150 from the first position 170 into the second position 172 in the rearward direction 136 may, as an example, be driven by pushing the compression element 150, specifically the annular protrusion 152, onto the skin portion of the user, thereby pushing the compression element 150 into the rearward direction 136 and, simultaneously, increasing the pressure in the body tissue of the user in the region of puncturing. The latter process is also referred to as "milking".

In FIGS. 9 and 10, in view similar to FIGS. 7 and 8, respectively, the process of the rearward movement of the compression element 150 is shown. As can be seen, during this movement, the mounting arms 160 are spread apart and, thus, the rearward ends 196 protrude from the housing 114 and form trigger portions 184. These trigger portions 184 may interact with a trigger 198 of an analytical device, such as a simple trigger 198 shown in the cross-sectional view of FIG. 10. As soon as the rearward end 196, which protrudes from the housing 114, hits the trigger 198, a puncture motion may be triggered. The trigger 198, which is shown in a simplified schematic view, may comprise any type of trigger mechanism known to the skilled person in the art of puncture elements. The trigger 198 may be made with a minimum trigger force which is given in any case when the compression element 150 is pressed onto the skin surface of a user, such that the triggering force if provided in any event of use. This trigger force at the same time may be the milking force which is necessary for expressing bodily fluid from the punctured skin. Thus, the compression element 150 simultaneously acts as a part of a trigger mechanism of the analytical device. By the triggering process, the annular protrusion 152 of the compression element 150 is pushed back into a position adapted for an appropriate puncture depth. This second position 172 may either be a fixed position or an adaptable position. Still, preferably, no mechanical force is exerted onto the housing 114 during the movement of the compression element 150, in order to avoid disturbances of the detection.

In FIGS. 11 and 12, in a view similar to the views given in FIGS. 7 and 8 or 9 and 10, respectively, a state of the sampling element 110 after the measurement is shown, which is a used state of the sampling element 110. In this state, the release actuator 188 has been withdrawn from the sampling element 110, and the mounting arms 160 are not spread apart any longer. The locking mechanism, again, is in a locked state, with the compression element 150 being in the second position 172. In this second position 172, the snap hooks 176, with their protrusions 178, snap into the second notches 182. However, as specifically may be seen in the cross-sectional view of FIG. 12, the rearward ends 196 of the mounting arms 160 protrude from the housing 114, forming a protrusion 200 indicating a used state of the sampling element 110. This is due to the fact that, as an example, a depth $d_2$ of the second notches 182 may be smaller than a depth $d_1$ of the first notches 180.

The protrusions 200 may be used in various ways. Thus, the protrusions 200 may simply indicate to a user that the sampling element 110 is a used sampling element and, thus, may indicate that a reuse shall be avoided. Additionally or alternatively, the protrusions 200 may be used for indicating the used state of the sampling elements 110 to an analytical device and/or in order to prevent a reuse of the sampling elements 110 in various ways. Thus, as an example, the analytical device may provide an appropriate transfer mechanism and/or may provide an appropriate receiving structure which, such as by abutting the protrusions 200, may mechanically prevent a used sampling element 110 from being brought into an application position within the analytical device. Thus, as an example, the analytical device may provide elastic blocking elements, similar to a fish trap, which allow for a used assembling element 110 to be removed from an application position of the analytical device but which prevents the used assembling element 110 to be returned into the application position. This simple blocking mechanism 202, which allows for removing the sampling element 110 from an analytical device in the forward direction 134 and, by abutting the protrusions 200 when attempting pushing back the used sampling element 110 in the rearward direction 136, is indicated symbolically in FIG. 12.

In FIGS. 13 through 16C, various views of an embodiment of an analytical device 204 are shown, which make use of the sampling element 110 as disclosed in FIGS. 1-12 above. The sampling element 110 may be part of the analytical device 204 or may be introduced into the analytical device 204 as an independent element. Further, one or more of the detector 144 as shown in FIG. 2, the trigger 198 as shown in FIG. 10 or the blocking mechanism 202 as shown in FIG. 12 may be part of the analytical device 204, too. The analytical device 204 may further comprise a housing, which is not shown in the figures. In FIGS. 13-15, the analytical device 204 is shown in various actuation states, whereas FIGS. 16A-16C, in a combined sequence of the images of FIGS. 13-15, show a complete sampling cycle. In the following, reference will be made to all of these figures.

The analytical device 204 comprises two types of actuators or interacting elements, which is at least one coupling element 206 and the release element 188. As outlined above, the release element 188, having the release element bars 190, is adapted for releasing the locking mechanism 168 of the sampling element 190. The coupling element 206 on the other hand is adapted to drive the puncture element 112 to perform a puncture motion. For the latter purpose, the coupling element may comprise one or more hooks 208 adapted for engaging with an appropriate opening 210 at a rearward end of the puncture element 112 (see FIG. 2). Thus, the coupling element 206 is adapted to enter through the actuator opening 128 of the housing 114, to engage with the puncture element 112, to drive the puncture element 112 to perform a puncture motion in the forward direction 134, thereby perforating a skin portion of the user, and, afterwards, retracting the puncture element 112 into the chamber 122, in order to safely restore the puncture element 112 within the chamber 122. For details of this mechanism, as an example, reference may be made to one or more of documents WO 2011/044971 A2, WO 2012/140027 A1 or WO 2012/089524 A1. Still, other types of interaction of the coupling element 206 with the puncture element 112 are feasible.

The coupling element 206 and the release element 188 may both be mounted movably in the longitudinal direction 120. Thus, preferably, both the coupling element 206 and the release element 188 may be mounted on a common guide 212, such as a linear guide. The guide 212 may comprise slide bars 214 or any other type of guiding. On the slide bars 214, two independent slide carriages 216, 218, may be mounted slideably in the longitudinal direction 120. Thus, a first slide carriage 216 may be provided, which carries the release elements 188. Further, a second slide carriage 218 may be provided which carries the coupling element 206. The slide bars 214 may be kept in place by one or more mounting elements 220, such as one or more mounting blocks. Thus, even though the actuators 188 or 206 are mounted movably on the same guide 212, they may be adapted to move independently, preferably linearly, in the longitudinal direction 120, by the slide carriages 216, 218, independently and parallel, preferably coaxially, moving on the slide bars 214.

The release element 188 and the coupling element 206 may be driven independently or, preferably, by using a link mechanism 222, as shown in the embodiment of FIGS. 13-16C. Thus, as an example, the link mechanism 222 may comprise at least one lever 224, the movement of which may be controlled by a shank 226 and the first slide carriage 216. the shank 226 may be coupled to and guided by a drive mechanism of the analytical device 204, such as a drive mechanism having an electrical motor and/or a drive mechanism having one or more spring-based elements, such as one or more releasable spring mechanisms as generally known in the art. By these types of drives, the shank 226 may be adapted to provide movements, which, at least partially, are directed in the forward direction 134 and/or the rearward direction 136, thereby pivoting the lever 224.

The lever 224 may be coupled to the release element 188 and the coupling element 206, preferably in a pivotable fashion. Thus, as can be seen in FIG. 13 and FIG. 16A, the lever 224 may be coupled to the first slide carriage 216, which is the slide carriage of the release element 188, by a first bearing pin 230 and, further, may be coupled to the second slide carriage 218, which is the slide carriage of the coupling element 206, by a second bearing pin 232. In order to provide the possibility of an independent movement of the slide carriages 216, 218, the coupling of the bearing pins 230, 232 to the lever 224 shall be such that a distance of the coupling points may vary. For this purpose, in the embodiment shown in FIG. 13, as an example, the first bearing pin 230 is guided in a further guide slot 234 of the lever 224, which, preferably, may be located at an opposing end to the end of the lever 224 comprising the guide slot 228. A distance between the shank 226 and the bearing pins 230, 232, may determine a lever ratio of the link mechanism 222. The lever ratio determines the movement of the first slide carriage 216, when the shank 226 and/or the first slide carriage 216 are moved.

In FIGS. 14 and 15, a preparation action (FIG. 14), implying releasing the locking mechanism 168, and a puncture action (FIG. 15) are shown in further detail. Thus, firstly, in FIG. 14 and FIG. 16B, a preparation action is shown, in order to prepare the sampling element 110 for sampling. For this purpose, the first slide carriage 216 is pushed forward. Thereby, as explained with regard to FIGS. 7 and 8 above, the release element bars 190 are forced in between the housing 114 and the mounting arms 160, thereby releasing the locking mechanism 168, as explained above. The movement of the first slide carriage 216 is simultaneously transmitted to the second slide carriage 218 by the link mechanism 222, here the lever 224. Thereby, the coupling element 206 enters the chamber 122 and engages with the puncture element 112 housed in there. The stagnant shank 226 acts in this preparation phase as a pivot axis for the lever 224. At the end of this phase the first slide carriage 216 is held in place.

Still, as shown in FIG. 14 and FIG. 16B, the compression element 150 is in the first position 170, even though the locking mechanism 168 is unlocked. By pressing the compression element 150, specifically the annular protrusion 152, onto the skin portion of the user, the compression element 150 is pushed in the rearward direction, and the trigger portion 184 of one or more of the mounting arms 160 may exert a trigger force onto a trigger 198 (not shown in FIG. 14, see e.g. FIG. 10). Thereby, a puncture action is triggered. During the puncture action, the first slide carriage 216 may maintain the position as shown in FIG. 14 which may keep the release actuator bars 190 forced in between the mounting arms 160 and the housing 114, in order to keep the compression element 150 freely movable with regard to the housing 114, wherein the latter preferably is kept in a fixed application position within the analytical device 204.

The puncture action is shown in FIG. 15 and FIG. 16C. As outlined above, the puncture action may be triggered by the trigger portion 184 of one or more of the mounting arms 160 when the compression element 150 is pushed into the second position 172, such as by pushing the annular protrusion 152 onto a skin portion of the user.

In order to perform a puncture motion, the shank 226 momentarily is pushed into the forward direction 134, as shown in FIG. 15 and FIG. 16C, such as by releasing a spring energy storage, such as by releasing a drive spring or any other lancing actuator which is known by one skilled in the art. By lever action, the movement of the shank 226 is transferred onto the second bearing pin 232 that is part of the second slide carriage 218 on which the coupling element 206 is mounted, which, consequently, is pushed forward, drives the tip 132 to perform a puncture motion, perforating a skin portion of the user. Then shank 226 is moved backward by which the tip 132 is retracted form the wound. Finally back in the rearward position shank 226 stands still again and now acts as a pivot axis for lever 224. Now the slide carriage 216 is pulled back into the rearward direction 136, e.g. it is released from its forward position and forced backward by a spring element 236, or it is driven by the preparation drive, and the coupling element 206 is retracted out of the housing 114. As outlined above, preferably, the puncture element 112 comprises one or more capillary elements, such as one or more capillary slits on one or more surfaces of the puncture element 112. The sample which is taken up by these capillary elements may fully or partially be transferred onto the test field 138, and an optical detection of a detection reaction, by using the detector 144, may take place.

Since the release element 188 is mounted to carriage 216 it also retracts and the locking mechanism 168 reengages, now in the second position 172.

It shall be noted that the drive mechanism shown in FIGS. 13-16C is only one of a plurality of driving mechanisms possible. Thus, other driving mechanisms may be used which provide both a release actuator 188 and a coupling element 206, in order to release the locking mechanism 168 in a preparation action and in order to drive the actual puncture motion.

| List of reference numbers | |
| --- | --- |
| 110 | sampling element |
| 112 | puncture element |
| 114 | housing |
| 116 | upper housing part |
| 118 | lower housing part |
| 120 | longitudinal axis |
| 122 | chamber |
| 124 | puncture opening |
| 126 | front face |
| 128 | actuator opening |
| 130 | rear face |
| 132 | tip |
| 134 | forward direction |
| 136 | rearward direction |
| 138 | test field |
| 140 | test chemical |
| 142 | detector opening |
| 144 | detector |
| 146 | light source |
| 148 | light-sensitive element |
| 150 | compression element |
| 152 | annular protrusion |
| 154 | compression opening |
| 156 | body |
| 158 | mounting portion |
| 160 | mounting arm |
| 162 | guiding |
| 164 | guide rail |
| 166 | side face |
| 168 | locking mechanism |
| 170 | first position |
| 172 | second position |
| 174 | snap arm |
| 176 | snap hooks |
| 178 | protrusions |
| 180 | first notch |
| 182 | second notch |
| 184 | trigger portion |
| 186 | clearance |
| 188 | release element |
| 190 | release element bar |
| 192 | wedge |
| 194 | guiding surface |
| 196 | rearward end |
| 198 | trigger |
| 200 | protrusion |
| 202 | blocking mechanism |
| 204 | analytical device |
| 206 | coupling element |
| 208 | hook |
| 210 | opening |
| 212 | guide |
| 214 | slide bar |
| 216 | first slide carriage |
| 218 | second slide carriage |
| 220 | mounting element |
| 222 | link mechanism |
| 224 | lever |
| 226 | shank |
| 228 | guide slot |
| 230 | first bearing pin |
| 232 | second bearing pin |
| 234 | guide slot |
| 236 | biasing spring element |

The invention claimed is:

1. A sampling element for generating a sample of a body fluid, the sampling element comprising:
   a housing comprising a chamber with at least one puncture element stored therein, wherein a tip of the puncture element is movable through at least one puncture opening of the housing in order to perforate a skin portion of a user;
   at least one compression element, wherein the compression element is adapted to increase a pressure of a body fluid within a body tissue of the user in a region of puncturing when pressed onto the skin portion of the user,
      wherein the compression element comprises a first, ring-shaped protrusion which fully or partially surrounds the puncture opening of the housing and is positioned to contact the skin portion of the user,
      wherein the compression element is movably mounted to the housing, the compression element having a first position prior to use of the sampling element, and a second position offset from the first position after use of the sampling element;
   a second protrusion positioned to prevent use of the sampling element when the compression element is in the second position; and
   a locking mechanism configured for releasably locking the compression element in the first position and for non-releasably locking the compression element in the second position.

2. The sampling element of claim 1, wherein the compression element comprises at least one trigger portion adapted to exert a trigger action onto a trigger of an analytical device using the sampling element when the compression element is moved from the first position into the second position.

3. The sampling element of claim 1, wherein the compression element comprises at least one annular protrusion being adapted to be pressed onto the skin portion in the region of puncturing, the compression element further comprising a mounting portion movably mounted to the housing, wherein the mounting portion comprises at least one mounting arm which is slidably guided in a guiding of the housing.

4. The sampling element of claim 1, wherein the locking mechanism comprises a releasable snap fit connection.

5. The sampling element of claim 1, wherein the compression element comprises at least one snap arm which is adapted to be releasably snapped into a first notch when the compression element is in the first position and is adapted to be snapped into a second notch when the compression element is in the second position.

6. The sampling element of claim 1, wherein the sampling element further comprises at least one test chemical adapted for performing at least one detectable detection reaction in the presence of at least one analyte to be detected, wherein the sampling element is adapted to transfer body fluid onto the test chemical.

7. A sampling element generating a sample of a body fluid and configured to be received within an analytical device for use, the sampling element comprising:
   a housing comprising a chamber with at least one puncture element stored therein, wherein a tip of the puncture element is moveable through at least one puncture opening of the housing in order to perforate a skin portion of a user;
   at least one compression element, wherein the compression element is adapted to increase a pressure of a body fluid within a body tissue of the user in a region of puncturing when pressed onto the skin portion of the user,
      wherein the compression element comprises a first, ring-shaped protrusion which fully or partially surrounds the puncture opening of the housing and is positioned to contact the skin portion of the user,
      wherein the compression element is movably mounted to the housing, the compression element having a first position prior to use of the sampling element, and a second position offset from the first position after use of the sampling element; and
   a second protrusion positioned to prevent use of the sampling element when the compression element is in the second position, the protrusion being positioned to prevent the sampling element from being received within the analytical device when the compression element is in the second position.

8. The sampling element of claim 7 in which the second protrusion does not extend outside of the housing when the compression element is in the first position, but does extend outside of the housing when the compression element is in the second position.

9. The sampling element of claim 8 in which the second protrusion is formed upon movement of the compression element from the first position to the second position.

10. The sampling element of claim 1 in which the sampling element is a single-use, disposable sampling element.

11. The A sampling element for generating a sample of a body fluid, the sampling element comprising:
   a housing comprising a chamber with at least one puncture element stored therein, wherein a tip of the puncture element is movable through at least one puncture opening of the housing in order to perforate a skin portion of a user;
   at least one compression element, wherein the compression element is adapted to increase a pressure of a body fluid within a body tissue of user in a region of puncturing when pressed onto the skin portion of the user,
      wherein the compression element comprises a first, ring-shaped protrusion which fully or partially surrounds the puncture opening of the housing and is positioned to contact the skin portion of the user,
      wherein the compression element is movably mounted to the housing, the compression element having a first position prior to use of the sampling element, and a second position offset from the first position after use of the sampling element; and
   the compression element further comprising a second protrusion positioned to prevent use of the sampling element when the compression element is in the second position, the protrusion protruding from the housing when the compression element is in the second position.

12. The sampling element of claim 1 in which the first position is a first position relative to the housing and in which the second position is a second position relative to the housing.

13. A sampling element for generating a sample of a body fluid, the sampling element comprising:
   a housing comprising a chamber with at least one puncture element stored therein, wherein a tip of the puncture element is movable through at least one puncture opening of the housing in order to perforate a skin portion of a user;

at least one compression element, where the compression element is adapted to increase a pressure of a body fluid within a body tissue of the user in a region of puncturing when pressed onto the skin portion of the user,
wherein the compression element comprises a first, ring-shaped protrusion which fully or partially surrounds the puncture opening of the housing and is positioned to contact the skin portion of the user,
wherein the compression element is movably mounted to the housing, the compression element having a first position prior to use of the sampling element, and a second position offset from the first position after use of the sampling element, the first position being a first position relative to the housing and the second position being a second position relative to the housing; and
a second protrusion positioned to prevent use of the sampling element when the compression element is in the second position,
the sampling element being a single-use, disposable sampling element.

14. The sampling element of claim 1 in which the second position is offset from the first position.

15. The sampling element of claim 7 in which the second position is offset from the first position.

16. The sampling element of claim 11 in which the second position is offset from the first position.

17. The sampling element of claim 13 in which the second position is offset from the first position.

* * * * *